United States Patent
Yi et al.

(10) Patent No.: US 11,316,198 B2
(45) Date of Patent: Apr. 26, 2022

(54) LITHIUM-ION BATTERY AND APPARATUS

(71) Applicant: Contemporary Amperex Technology Co., Limited, Fujian (CN)

(72) Inventors: Tiancheng Yi, Ningde (CN); Chunhua Hu, Ningde (CN); Yao Jiang, Ningde (CN); Shushi Dou, Ningde (CN); Chengdu Liang, Ningde (CN)

(73) Assignee: Contemporary Amperex Technology Co., Limited, Ningde (CN)

( * ) Notice: Subject to any disclaimer, the term of this patent is extended or adjusted under 35 U.S.C. 154(b) by 0 days.

(21) Appl. No.: 17/144,517

(22) Filed: Jan. 8, 2021

(65) Prior Publication Data

US 2021/0143476 A1 May 13, 2021

Related U.S. Application Data

(63) Continuation of application No. PCT/CN2019/125325, filed on Dec. 13, 2019.

(30) Foreign Application Priority Data

Dec. 14, 2018 (CN) .......................... 201811537016.0

(51) Int. Cl.
| | | |
|---|---|---|
| *H01M 10/0567* | (2010.01) | |
| *C07D 239/04* | (2006.01) | |
| *C07D 241/04* | (2006.01) | |
| *C07D 251/04* | (2006.01) | |
| *H01M 4/525* | (2010.01) | |
| *H01M 10/0525* | (2010.01) | |

(52) U.S. Cl.
CPC ...... *H01M 10/0567* (2013.01); *C07D 239/04* (2013.01); *C07D 241/04* (2013.01); *C07D 251/04* (2013.01); *H01M 4/525* (2013.01); *H01M 10/0525* (2013.01); *H01M 2220/20* (2013.01); *H01M 2300/0025* (2013.01)

(58) Field of Classification Search
None
See application file for complete search history.

(56) References Cited

U.S. PATENT DOCUMENTS

| | | |
|---|---|---|
| 2004/0142240 A1 | 7/2004 | Nagayama et al. |
| 2015/0064578 A1* | 3/2015 | Kang ............... H01M 10/0567 429/341 |
| 2017/0069934 A1 | 3/2017 | Kim et al. |

FOREIGN PATENT DOCUMENTS

| | | |
|---|---|---|
| CN | 103022556 A | 4/2013 |
| CN | 103518285 A | 1/2014 |
| CN | 103618081 A | 3/2014 |
| CN | 103078140 B | 4/2015 |
| CN | 105655639 A | 6/2016 |
| CN | 105680088 A | 6/2016 |
| CN | 106356561 A | 1/2017 |
| CN | 109148950 A | 1/2019 |
| CN | 109216764 A | 1/2019 |
| CN | 109256585 A | 1/2019 |
| CN | 110391460 A | 10/2019 |
| EP | 2 367 230 B1 | 12/2014 |
| EP | 3279998 A1 | 2/2018 |
| JP | H11 111332 A | 4/1999 |
| JP | 2001 357877 A | 12/2001 |
| JP | 2012104439 A | 5/2012 |
| KR | 2015 0138813 A | 12/2015 |

OTHER PUBLICATIONS

Search Report dated Mar. 12, 2020 in corresponding International Application No. PCT/CN2019/125325; 8 pages.
Chinese Office Action dated Dec. 25, 2020 in corresponding application No. 201811537016.0, 8 pgs.
Written Opinion dated Mar. 12, 2020 in corresponding International Application No. PCT/CN2019/125325; 12 pages.
European Search Report dated Aug. 25, 2021 in corresponding European Application No. EP19895607.

* cited by examiner

*Primary Examiner* — Laura Weiner
(74) *Attorney, Agent, or Firm* — Maier & Maier, PLLC

(57) ABSTRACT

The present application provides a lithium-ion battery and an apparatus, the lithium-ion battery includes an electrode assembly and an electrolyte. The electrode assembly includes a positive electrode sheet, a negative electrode sheet and a separation film. The positive active material in the positive electrode sheet includes $Li_{x1}Co_{y1}M_{1-y1}O_{2-z1}Q_{z1}$, $0.5 \leq x1 \leq 1.2$, $0.8 \leq y1 < 1.0$, $0 \leq z1 \leq 0.1$, and M is selected from one of Al, Ti, Zr, Y, and Mg, and Q is selected from one or more of F, Cl, and S. The electrolyte contains an additive A and an additive B, the additive A is a polynitrile six-membered nitrogen-heterocyclic compound with a relatively low oxidation potential, and the additive B is an aliphatic dinitrile or polynitrile compound with a relatively high oxidation potential. The lithium-ion battery of the present application has superb cycle performance and storage performance, especially under high-temperature and high-voltage conditions.

10 Claims, 5 Drawing Sheets

LITHIUM-ION BATTERY AND APPARATUS

CROSS-REFERENCE TO RELATED APPLICATIONS

The present application is a continuation of International Application No. PCT/CN2019/125325, filed on Dec. 13, 2019, which claims priority to Chinese Patent Application No. 201811537016.0, filed on Dec. 14, 2018, both of which are hereby incorporated by reference in their entireties.

TECHNICAL FIELD

The present application relates to the field of energy storage materials, and in particular, to a lithium-ion battery and an apparatus.

BACKGROUND

Lithium-ion batteries are widely applied to electromobiles and consumer electronic products due to their advantages such as high energy density, high output power, long cycle life and low environmental pollution. Current requirements on lithium-ion batteries are high voltage, high power, long cycle life, long storage life and superb safety performance.

Currently, $LiCoO_2$ is widely used as a positive active material in lithium-ion batteries and shows relatively stable performance during cycling between fully discharged $LiCoO_2$ and semi-charged $Li_{0.5}CoO_2$ (4.2 V vs. Li). Therefore, lithium ions that are actually used account only for ½ of lithium ions actually contained in $LiCoO_2$. When the voltage is greater than 4.2 V, the remaining ½ of lithium ions contained in $LiCoO_2$ may continue to be extracted. However, during deep delithiation, $Co^{3+}$ is oxidized into quite unstable $Co^{4+}$, which oxidizes an electrolyte together with surface oxygen that loses a large quantity of electrons. In this case, a large amount of gas is produced inside the batteries, causing the batteries to swell. In addition, due to a corrosive effect of HF in the electrolyte on a surface of a positive electrode, $Co^{4+}$ is dissolved in the electrolyte and deposited on a surface of a negative electrode, catalyzing reduction of the electrolyte, and also producing a large amount of gas that causes the batteries to swell. In addition, due to high overlapping between a 3d energy level of Co and a 2p energy level of O, the deep delithiation also causes lattice oxygen to lose a large quantity of electrons, resulting in sharp shrinkage of $LiCoO_2$ unit cells along a c-axis direction, and leading to instability or even collapse of a local bulk structure. This eventually causes loss of $LiCoO_2$ active sites, and a rapid decrease in capacity of the lithium-ion batteries. Therefore, $LiCoO_2$ has very poor performance when being used in a high-voltage system greater than 4.2 V.

In view of this, the present application is hereby proposed.

SUMMARY

In view of the problems in the background, an object of the present application is to provide a lithium-ion battery and an apparatus. The lithium-ion battery has superb cycle performance and storage performance, especially under high-temperature and high-voltage conditions.

In order to achieve the abovementioned object, in a first aspect, the present application provides a lithium-ion battery, including an electrode assembly and an electrolyte. The electrode assembly includes a positive electrode sheet, a negative electrode sheet, and a separation film. A positive active material of the positive electrode sheet includes $Li_{x1}Co_{y1}M_{1-y1}O_{2-z1}Q_{z1}$, where $0.5 \leq x1 \leq 1.2$, $0.8 \leq y1 < 1.0$, $0 \leq z1 \leq 0.1$, M is selected from one or more of Al, Ti, Zr, Y, and Mg, Q is selected from one or more of F, Cl and S. The electrolyte contains an additive A and an additive B. The additive A is selected from one or more of compounds represented by Formula I-1, Formula I-2, and Formula I-3, and the additive B is selected from one or more of compounds represented by Formula II-1 and Formula II-2.

In the Formula I-1, the Formula I-2, and the Formula I-3: $R_1$, $R_2$, $R_3$, and $R_4$ each are independently selected from a hydrogen atom, a halogen atom, a substituted or unsubstituted $C_1$-$C_{12}$ alkyl group, a substituted or unsubstituted $C_1$-$C_{12}$ alkoxy group, a substituted or unsubstituted $C_1$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, a substituted or unsubstituted $C_2$-$C_{12}$ heterocyclic group, where a substituent group is selected from one or more of a halogen atom, a nitrile group, a C1-C6 alkyl group, a $C_2$-$C_6$ alkenyl group, a $C_1$-$C_6$ alkoxy group; x, y, and z each are independently selected from integers 0-8; and m, n, and k each are independently selected from integers 0-2.

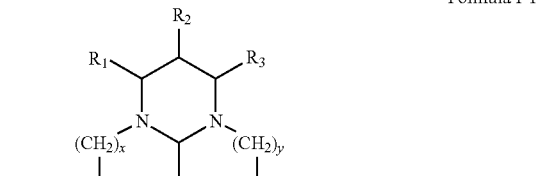

Formula I-1

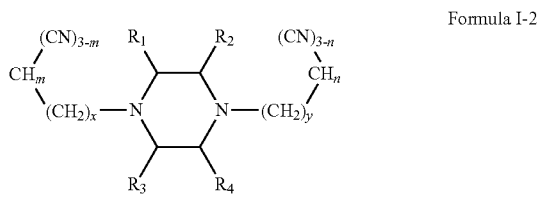

Formula I-2

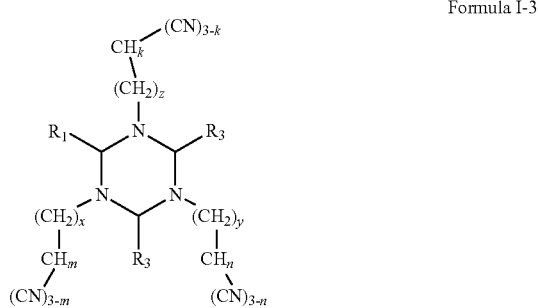

Formula I-3

In the Formula II-1 and Formula II-2: $R_5$ is selected from a substituted or unsubstituted $C_1$-$C_{12}$ alkylene group, a substituted or unsubstituted $C_2$-$C_{12}$ alkenylene group, a substituted or unsubstituted $C_2$-$C_{12}$ alkynylene group, $R_6$, $R_7$, and $R_8$ each are independently selected from substituted or unsubstituted $C_0$-$C_{12}$ alkylene group, substituted or unsubstituted $C_2$-$C_{12}$ alkenylene group, substituted or unsubstituted $C_2$-$C_{12}$ alkynylene group, where the substituent group is selected from one or more of a halogen atom, a nitrile group, a $C_1$-$C_6$ alkyl group, a $C_2$-$C_6$ alkenyl group, and a $C_1$-$C_6$ alkoxy group.

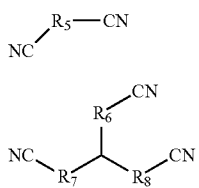

Formula II-1

Formula II-2

In a second aspect in of the present application, the present application provides an apparatus, including the lithium-ion battery described in the first aspect of the present application.

Compared with the prior art, the present application includes at least the following beneficial effects:

In the present application, a positive active material that contains a metal ion M-doped lithium cobalt oxide material $Li_{x1}Co_{y1}M_{1-y1}O_{2-z1}Q_{z1}$ is used, where the doping element M serves as a framework in the lithium cobalt oxide material. This could reduce lattice deformation of the lithium cobalt oxide material during deep delithiation, delay degradation of bulk structure of the lithium cobalt oxide material, and improve structural stability of the lithium-ion battery when the lithium-ion battery is used at a high voltage greater than 4.2 V.

The electrolyte of the present application includes a combined additive of the additive A and the additive B. The additive A is a polynitrile six-membered nitrogen-heterocyclic compound with a relatively low oxidation potential, such that a stable complex layer can be formed on a surface of the positive active material during formation of the battery. This could effectively passivate the surface of the positive active material and inhibit its oxidation effect on the electrolyte, and reduce gas production of the battery; the electrolyte of the present application further includes aliphatic dinitrile or polynitrile compounds with a relatively high oxidation potential, which can stably exist in the electrolyte for a long time, and can repair the damaged complex layer at any time during cycling or high-temperature storage, reduce dissolution of transition metal ions, and greatly reduce damage of the transition metal to the SEI film deposited on the negative electrode after dissolution; therefore, the electrolyte of the present application can improve the cycle performance and storage performance of lithium-ion batteries, especially improve the cycle performance and storage performance of lithium-ion batteries under of high-temperature and high-voltage conditions. The apparatus of the present application includes the lithium-ion battery described in the first aspect of the present application, and therefore provides at least the same advantages as the lithium-ion battery.

DETAILED DESCRIPTION OF EMBODIMENTS

Figure 1:
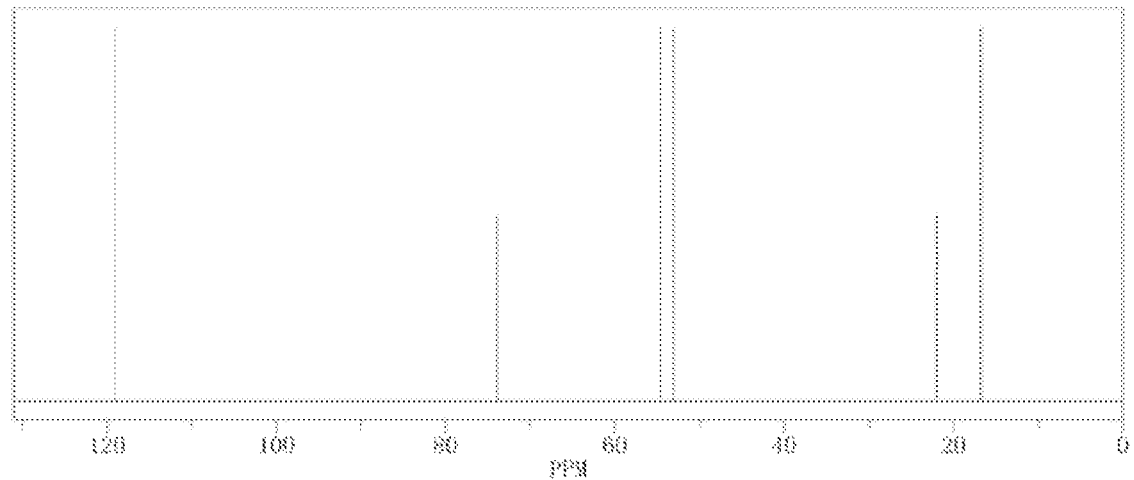
FIG. 1 is a carbon nuclear magnetic resonance spectrum of a compound A1.

A lithium-ion battery and an apparatus according to the present application are described in detail below.

First, the lithium-ion battery according to the first aspect of the present application is described.

The lithium-ion battery according to the present application includes an electrode assembly and an electrolyte. The electrode assembly includes a positive electrode sheet, a negative electrode sheet, and a separation film.

Where, a positive active material in the positive electrode sheet includes $Li_{x1}Co_{y1}M_{1-y1}O_{2-z1}Q_{z1}$, where $0.5 \leq x1 \leq 1.2$, $0.8 \leq y1 < 1.0$, $0 \leq z1 \leq 0.1$, M is selected from one or more of Al, Ti, Zr, Y, and Mg, and Q is selected from one or more of F, Cl, and S. The electrolyte includes an additive A and an additive B, the additive A is selected from one or more of compounds represented by Formula I-1, Formula I-2 and Formula I-3, and the additive B is selected from one or more of compounds represented by Formula II-1 and Formula II-2.

In the Formula I-1, the Formula I-2, and the Formula I-3: $R_1$, $R_2$, $R_3$, and $R_4$ each are independently selected from a hydrogen atom, a halogen atom, substituted or a unsubstituted $C_1$-$C_{12}$ alkyl group, a substituted or unsubstituted $C_1$-$C_{12}$ alkoxy group, a substituted or unsubstituted $C_1$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, a substituted or unsubstituted $C_2$-$C_{12}$ heterocyclic group, where a substituent group (indicating a substitution case in the "substituted or unsubstituted" herein) is selected from one or more of a halogen atom, a nitrile group, a $C_1$-$C_6$ alkyl group, a $C_2$-$C_6$ alkenyl group and a $C_1$-$C_6$ alkoxy group; x, y, and z each are independently selected from integers 0-8; and m, n, and k each are independently selected from integers 0-2.

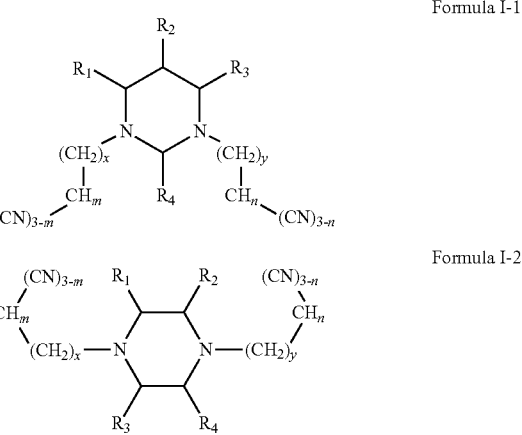

Formula I-1

Formula I-2

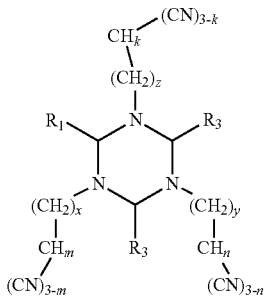

Formula I-3

In the Formula II-1 and the Formula II-2: $R_5$ is selected from a substituted or unsubstituted $C_1$-$C_{12}$ alkylene group, a substituted or unsubstituted $C_2$-$C_{12}$ alkenylene group, a substituted or unsubstituted $C_2$-$C_{12}$ alkynylene group, $R_6$, $R_7$, and $R_8$ each are independently selected from a substituted or unsubstituted $C_0$-$C_{12}$ alkylene group, a substituted or unsubstituted $C_2$-$C_{12}$ alkenylene group, a substituted or unsubstituted $C_2$-$C_{12}$ alkynylene group, where the substituent group (indicating a substitution case in the "substituted or unsubstituted" herein) is selected from one or more of a halogen atom, a nitrile group, a $C_1$-$C_6$ alkyl group, a $C_2$-$C_6$ alkenyl group, and a $C_1$-$C_6$ alkoxy group.

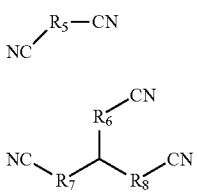

Formula II-1

Formula II-2

The lithium-ion battery of the present application has superb cycle performance and storage performance, especially under high-temperature and high-voltage conditions. On the one hand, in the present application, a positive active material that contains a metal ion M-doped lithium cobalt oxide material $Li_{x1}Co_{y1}M_{1-y1}O_{2-z1}Q_{z1}$ is used, where the doping element M serves as a framework in the lithium cobalt oxide material. This could reduce lattice deformation of the lithium cobalt oxide material during deep delithiation, delay degradation of bulk structure of the lithium cobalt oxide material, and improve structural stability of the lithium-ion battery when the lithium-ion battery is used at a high voltage greater than 4.2 V. On the other hand, the additive A and the additive B are added into the electrolyte of the present application at the same time, and the two can play a synergistic effect to protect the lithium-ion battery together, and make the lithium-ion battery have superb cycle performance and storage performance, especially under high-temperature and high-voltage conditions.

Specifically:

the additive A is a polynitrile six-membered nitrogen-heterocyclic compound with a relatively low oxidation potential. Nitrogen atoms in the nitrile groups contain lone pair electrons, which have relatively strong complexation with a transition metal in the positive active material. After being applied in the electrolyte, the additive A may be adsorbed on a surface of the positive active material during formation of the battery to form a loose porous protective film during the formation of the battery and effectively passivate the surface of the positive active material. The porous protective film can not only isolate the surface of the positive active material from direct contact with the electrolyte without affecting the normal transmission of ions, but also can reduce the surface activity of the positive active material while inhibiting a large number of side reactions on the surface of the positive active material, thereby achieving the effect of decreasing side reaction products and reducing gas production.

The additive A has a special six-membered nitrogen-heterocyclic structure. A spacing between nitrile groups is closer to that between transition metals on the surface of the positive active material. This could maximize complexation of the nitrile groups and allow more nitrile groups to have a complexation effect. Therefore, compared with a conventional linear nitrile compound, the polynitrile six-membered nitrogen-heterocyclic compound in the present application has a better passivation effect.

The special six-membered nitrogen-heterocyclic structure of the additive A in this application can further lower an oxidation potential of molecules, so that a stable complex layer may be formed on the surface of the positive active material during formation of the battery. This may help improve electrochemical performance of an entire battery system, for example, by reducing gas production and extending a cycle life under high-temperature and high-voltage conditions.

The additive B is an aliphatic dinitrile or polynitrile compound. An aliphatic framework has strong oxidation resistance and can exist stably for a long time after being added to the electrolyte. Nitrogen atoms in the nitrile groups contain lone pair electrons, which have relatively strong complexation with a transition metal in the positive active material, and can repair the damaged complex layer (formed by the additive A) at any time during cycling or high-temperature storage, reduce dissolution of transition metal ions, and greatly reduce the damage of the transition metal to the SEI film deposited on the negative electrode after dissolution. Therefore, when the additive B is applied to the electrolyte, the lithium-ion battery has superb high temperature and high voltage cycle performance and storage performance.

In the lithium-ion battery of this application, preferably, based on total mass of the electrolyte, mass percent of the additive A is 0.1%-10%. If the amount of the additive A is too low, improvement made by the additive A to the electrolyte is not obvious; if the amount of the additive A is too high, the complex layer formed by the additive A being adsorbed on the surface of the positive active material would be too thick and dense, affecting diffusion and migration of lithium ions, and greatly increasing positive electrode impedance. In addition, excessively high amount of the additive A further causes an increase in overall viscosity of the electrolyte and a decrease in an ionic conductivity, and therefore, affects performance of the lithium-ion battery. An upper limit of the amount of the additive A may be any one selected from 10%, 9%, 8%, 7%, 6%, 5%, 4.5%, 4%, 3.5%, 3%, 2.5%, 2%, 1.5%, 1%, or 0.8%, and a lower limit of the amount of the additive A may be any one selected from 0.1%, 0.2%, 0.3%, 0.4%, 0.5%, 0.6%, 0.7%, 0.8%, 0.9%, 1.0%, or 1.2%.

Even more preferably, based on the total mass of the electrolyte, the mass percent of the additive A is 0.1%-3.5%.

In the lithium-ion battery of this application, preferably, based on total mass of the electrolyte, mass percent of the additive B is 0.1%-10%. If an amount of the additive B is too low, the repairing effect on the complex layer formed by the additive A is not obvious; if the amount of the additive B is too high, the complex layer formed on the surface of the positive active material is too thick and too dense, which greatly increase impedance of the negative electrode, and adversely affects the performance of the lithium-ion battery. An upper limit of the amount of the additive B may be selected from any one of 10%, 9%, 8%, 7%, 6%, 5%, 4.5%, 4%, 3.5%, 3%, 2.5%, 2%, 1.5%, 1%, 0.8%, and a lower limit of the amount of the additive B may be selected from any one of 0.1%, 0.2%, 0.3%, 0.4%, 0.5%, 0.6%.

Even more preferably, based on the total mass of the electrolyte, the mass percent of the additive B is 0.1% to 5%.

In the lithium-ion battery of the present application, in the compounds represented by the Formula I-1, the Formula I-2, and the Formula I-3:

the $C_1$-$C_{12}$ alkyl group can be a chain alkyl group or a cyclic alkyl group. The chain alkyl group may be a straight chain alkyl group or a branched chain alkyl group, and hydrogen on a ring of the cyclic alkyl group may be further substituted by an alkyl group. A preferable lower limit of a quantity of carbon atoms in the $C_1$-$C_{12}$ alkyl group is 1, 2, 3, 4, and 5, and a preferable upper limit is 3, 4, 5, 6, 8, 10, or 12. Preferably, a $C_1$-$C_{10}$ alkyl group is selected. More preferably, a $C_1$-$C_6$ chain alkyl group, or a $C_3$-$C_8$ cyclic alkyl group is selected. Furthermore preferably, a $C_1$-$C_4$ chain alkyl group, or a $C_5$-$C_7$ cyclic alkyl group is selected. Examples of the $C_1$-$C_{12}$ alkyl group may specifically include a methyl group, an ethyl group, an n-propyl group, isopropyl group, an n-butyl group, an isobutyl group, a sec-butyl group, a tert-butyl group, an n-pentyl group, an isopentyl group, a neopentyl group, a hexyl group, a 2-methyl-pentyl group, a 3-methyl-pentyl group, a 1,1,2-trimethyl-propyl group, a 3,3-dimethyl-butyl group, a heptyl group, a 2-heptyl group, a 3-heptyl group, a 2-methylhexyl group, a 3-methylhexyl group, an isoheptyl group, an octyl group, a nonyl group, and a decyl group.

When the aforementioned $C_1$-$C_{12}$ alkyl group contains oxygen atoms, the $C_1$-$C_{12}$ alkyl group may be a $C_1$-$C_{12}$ alkoxy group. Preferably, a $C_1$-$C_{10}$ alkoxy group is selected. More preferably, a $C_1$-$C_6$ alkoxy group is selected. Furthermore preferably, a $C_1$-$C_4$ alkoxy group is selected. Examples of the $C_1$-$C_{12}$ alkoxy group may specifically include a methoxy group, an ethoxy group, an n-propoxy group, an isopropoxy group, an n-butoxy group, a sec-butoxy group, a t-butoxy group, an n-pentyloxy group, an isopentyloxy group, a cyclopentyloxy group, and a cyclohexyloxy group.

The $C_2$-$C_{12}$ alkenyl group may be a cyclic alkenyl group or a chain alkenyl group, and the chain alkenyl group may be a linear alkenyl group or a branched alkenyl group. In addition, preferably, the $C_2$-$C_{12}$ alkenyl group has one double bond. A preferred lower limit of the quantity of carbon atoms in the $C_2$-$C_{12}$ alkenyl group is 2, 3, 4, or 5, and a preferred upper limit is 3, 4, 5, 6, 8, 10, or 12. Preferably, a $C_2$-$C_{10}$ alkenyl group is selected. More preferably, a $C_2$-$C_6$ alkenyl group is selected. Furthermore preferably, a $C_2$-$C_5$ alkenyl group is selected. Examples of the $C_2$-$C_{12}$ alkenyl group may specifically include a vinyl group, an allyl group, an isopropenyl group, a pentenyl group, a cyclohexenyl group, a cycloheptenyl group, and a cyclooctenyl group.

The $C_2$-$C_{12}$ alkynyl group may be a cyclic alkynyl group or a chain alkynyl group, and the chain alkynyl group may be a linear alkynyl group or a branched alkynyl group. In addition, preferably, the $C_2$-$C_{12}$ alkynyl group has one triple bond. A preferred lower limit of the quantity of carbon atoms in the $C_2$-$C_{12}$ alkynyl group is 2, 3, 4, or 5, and a preferred upper limit is 3, 4, 5, 6, 8, 10, or 12. Preferably, a $C_2$-$C_{10}$ alkynyl group is selected. More preferably, a $C_2$-$C_6$ alkynyl group is selected. Furthermore preferably, a $C_2$-$C_5$ alkynyl group is selected. Examples of the $C_2$-$C_{12}$ alkynyl group may specifically include an ethynyl group, a propargyl group, an isopropynyl group, a pentynyl group, a cyclohexynyl group, a cycloheptynyl group, and a cyclooctynyl group.

The $C_1$-$C_{12}$ amine group may be selected from

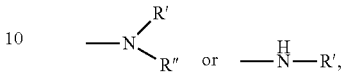

where R' and R" are selected from the $C_1$-$C_{12}$ alkyl group.

The $C_6$-$C_{26}$ aryl group may be a phenyl group, a phenylalkyl group, a biphenyl group, or a fused ring aromatic hydrocarbon group (for example, a naphthyl group, an anthracenyl group, or a phenanthrenyl group). The biphenyl group and the fused ring aromatic hydrocarbon group may be further substituted with an alkyl group or an alkenyl group. Preferably, a $C_6$-$C_{16}$ aryl group is selected. More preferably, a $C_6$-$C_{14}$ aryl group is selected. Furthermore preferably, a $C_6$-$C_9$ aryl group is selected. Examples of the $C_6$-$C_{26}$ aryl group may specifically include a phenyl group, a benzyl group, a biphenyl group, a p-tolyl group, an o-tolyl group, an m-tolyl group, a naphthyl group, an anthracenyl group, and a phenanthryl group.

A hetero atom in the $C_2$-$C_{12}$ heterocyclic group may be selected from one or more of oxygen, nitrogen, sulfur, phosphorus, and boron, and a heterocyclic ring may be an aliphatic heterocyclic ring or an aromatic heterocyclic ring. Preferably, a $C_2$-$C_{10}$ heterocyclic group is selected. More preferably, a $C_2$-$C_7$ heterocyclic group is selected. Furthermore preferably, a five-membered aromatic heterocyclic ring, a six-membered aromatic heterocyclic ring, and a benzo heterocyclic ring are selected. Examples of the $C_2$-$C_{12}$ heterocyclic group may specifically include an ethylene oxide group, a propylene oxide group, an ethylene sulfide group, an aziridine group, a β-propiolactone group, a furyl group, a thienyl group, a pyrrolyl group, a thiazolyl group, an imidazolyl group, a pyridyl group, a pyrazinyl group, a pyrimidinyl group, a pyridazinyl group, an indolyl group, and a quinolinyl group.

The halogen atom used as a substituent group may be selected from one or more of a fluorine atom, a chlorine atom, and a bromine atom. Preferably, the halogen atom is a fluorine atom.

(1) Specifically, the compound represented by the Formula I-1 is a polynitrile compound.

In the Formula I-1:

Preferably, $R_1$, $R_2$, $R_3$, and $R_4$ each are independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxy group, a substituted or unsubstituted $C_1$-$C_6$ amine group, a substituted or unsubstituted $C_2$-$C_6$ alkenyl group, a substituted or unsubstituted $C_2$-$C6$ alkynyl group, a substituted or unsubstituted $C_6$-$C_{12}$ aryl group, or a substituted or unsubstituted $C_2$-$C_{12}$ heterocyclic group. More preferably, $R_1$, $R_2$, $R_3$, and $R_4$ each are independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxy group, a substituted or unsubstituted $C_1$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group. The substituent group is selected from one or more of halogen atoms.

Preferably, x is selected from integers 0-6; more preferably, is selected from integers 0-4; furthermore preferably, is selected from 0, 1, or 2.

Preferably, y is selected from integers 0-6; more preferably, is selected from integers 0-4; furthermore preferably, is selected from 0, 1, or 2.

Preferably, m is selected from 1 or 2. Preferably, n is selected from 1 or 2.

Preferably, $R_1$ and $R_3$ are same groups. More preferably, $R_1$, $R_3$, and $R_4$ are all same groups.

Preferably, $R_1$ and $R_3$ are both hydrogen atoms. More preferably, $R_1$, $R_3$, and $R_4$ are all hydrogen atoms.

Preferably, $R_1$, $R_2$, $R_3$, and $R_4$ are all hydrogen atoms; or $R_1$, $R_3$, and $R_4$ are all hydrogen atoms, and $R_2$ is selected from a fluorine atom, a chlorine atom, a bromine atom, a substituted or unsubstituted $C_1$-$C_6$ linear or branched alkyl group, or a substituted or unsubstituted $C_1$-$C_6$ alkoxy group. The substituent group is selected from one or more of halogen atoms. Preferably, the substituent group is selected from a fluorine atom.

Preferably, the compound represented by the Formula I-1 may be specifically selected from one or more of the following compounds, but the present application is not limited to thereto:

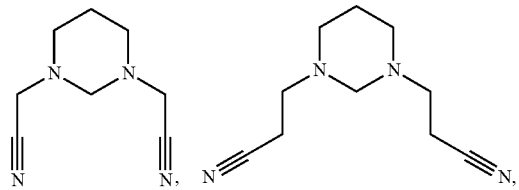

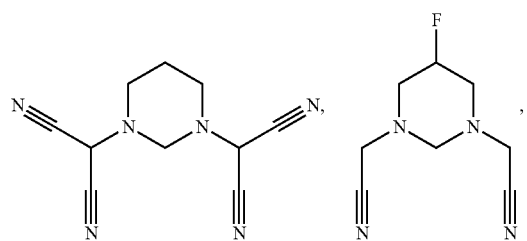

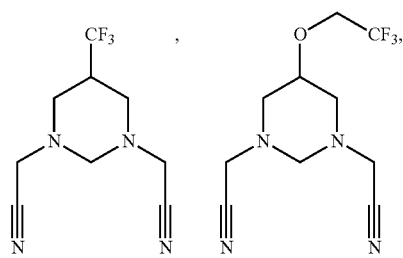

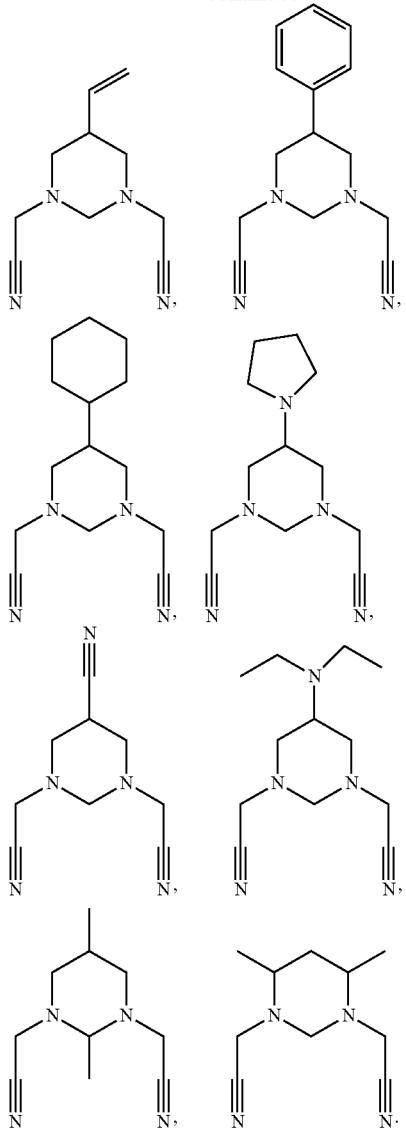

(2) Specifically, the compound represented by the Formula I-2 is a polynitrile piperazine compound.

In the Formula I-2:

Preferably, $R_1$, $R_2$, $R_3$, and $R_4$ each are independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxy group, a substituted or unsubstituted $C_1$-$C_6$ amine group, a substituted or unsubstituted $C_2$-$C_6$ alkenyl group, a substituted or unsubstituted $C_2$-C6 alkynyl group, a substituted or unsubstituted $C_6$-$C_{12}$ aryl group, or a substituted or unsubstituted $C_2$-$C_{12}$ heterocyclic group. More preferably, $R_1$, $R_2$, $R_3$, and $R_4$ each are independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxy group, a substituted or unsubstituted $C_1$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group. The substituent group is selected from one or more of halogen atoms.

Preferably, x is selected from integers 0-6; more preferably, is selected from integers 0-4; furthermore preferably, is selected from 0, 1, or 2. Preferably, y is selected from integers 0-6; more preferably, is selected from integers 0-4; furthermore preferably, is selected from 0, 1, or 2.

Preferably, m is selected from 1 or 2. Preferably, n is selected from 1 or 2.

Preferably, at least two of $R_1$, $R_2$, $R_3$, and $R_4$ are same groups. More preferably, at least three of $R_1$, $R_2$, $R_3$, and $R_4$ are same groups.

Preferably, at least two of $R_1$, $R_2$, $R_3$, and $R_4$ are hydrogen atoms. More preferably, at least three of $R_1$, $R_2$, $R_3$, and $R_4$ are hydrogen atoms.

Preferably, $R_1$, $R_2$, $R_3$, and $R_4$ are all hydrogen atoms; or three of $R_1$, $R_2$, $R_3$, and $R_4$ are hydrogen atoms, and the remaining one is selected from a fluorine atom, a chlorine atom, a bromine atom, a substituted or unsubstituted $C_1$-$C_6$ linear or branched alkyl group, or a substituted or unsubstituted $C_1$-$C_6$ alkoxy group. The substituent group is selected from one or more of halogen atoms. Preferably, the substituent group is selected from a fluorine atom.

Preferably, the compound represented by the Formula I-2 may be specifically selected from one or more of the following compounds, but the present application is not limited thereto:

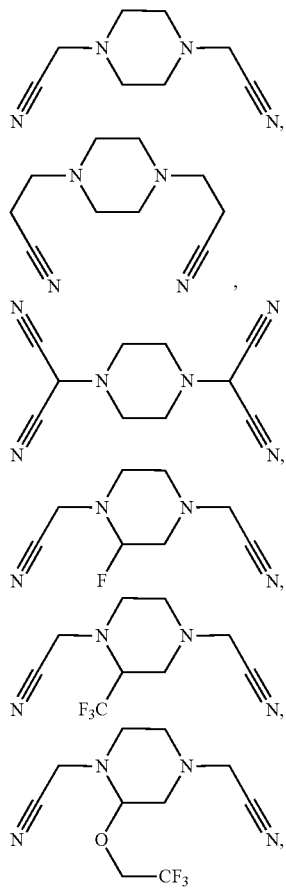

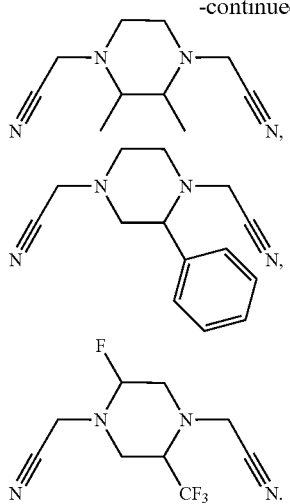

(3) Specifically, the compound represented by the Formula I-3 is a polynitrile s-triazine compound.

In the Formula I-3:

Preferably, $R_1$, $R_2$, and $R_3$ each are independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxy group, a substituted or unsubstituted $C_1$-$C_6$ amine group, a substituted or unsubstituted $C_2$-$C_6$ alkenyl group, a substituted or unsubstituted $C_2$-$C6$ alkynyl group, a substituted or unsubstituted $C_6$-$C_{12}$ aryl group, or a substituted or unsubstituted $C_2$-$C_{12}$ heterocyclic group. More preferably, $R_1$, $R_2$, and $R_3$ each are independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxy group, a substituted or unsubstituted $C_1$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, or a substituted or unsubstituted $C_2$-$C_7$ heterocyclic group. The substituent group is selected from one or more of halogen atoms.

Preferably, x is selected from integers 0-6; more preferably, is selected from integers 0-4; furthermore preferably, is selected from 0, 1, or 2. Preferably, y is selected from integers 0-6; more preferably, is selected from integers 0-4; furthermore preferably, is selected from 0, 1, or 2. Preferably, z is selected from integers 0-6; more preferably, is selected from integers 0-4; furthermore preferably, is selected from 0, 1, or 2.

Preferably, m is selected from 1 or 2. Preferably, n is selected from 1 or 2. Preferably, k is selected from 1 or 2.

Preferably, at least two of $R_1$, $R_2$, and $R_3$ are same groups.

Preferably, at least two of $R_1$, $R_2$, and $R_3$ are hydrogen atoms.

Preferably, $R_1$, $R_2$, and $R_3$ are all hydrogen atoms; or two of $R_1$, $R_2$, and $R_3$ are hydrogen atoms, and the remaining one is selected from a fluorine atom, a chlorine atom, a bromine atom, a substituted or unsubstituted $C_1$-$C_6$ linear or branched alkyl group, or a substituted or unsubstituted $C_1$-$C_6$ alkoxy group. The substituent group is selected from one or more of halogen atoms. Preferably, the substituent group is selected from a fluorine atom.

Preferably, the compound represented by the Formula I-3 may be specifically selected from one or more of the following compounds, but this application is not limited thereto:

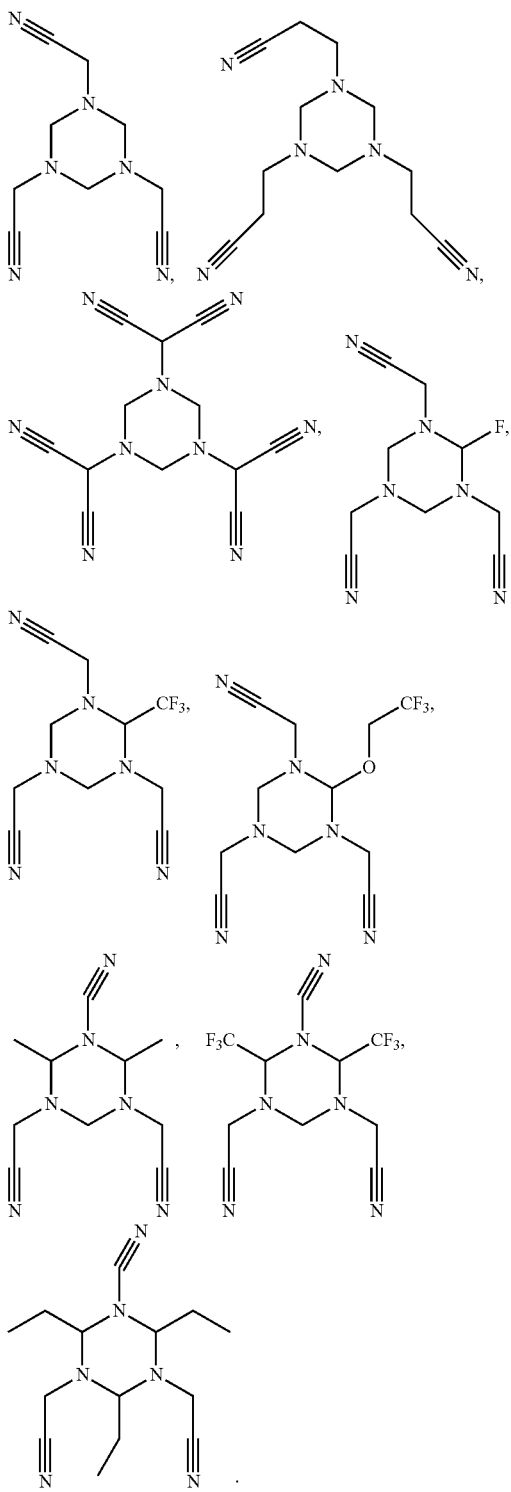

In the lithium-ion battery of the present application, in the compounds represented by the Formula II-1 and the Formula II-2:

The $C_0$-$C_{12}$ alkylene group may be a straight chain alkylene group or a branched chain alkylene group. A preferable lower limit of a quantity of carbon atoms in the $C_0$-$C_{12}$ alkylene group is 1, 2, 3, 4, and 5, a preferable upper limit is 3, 4, 5, 6, 7, 8, 9, 10, 11, 12. Preferably, a $C_0$-$C_{10}$ alkylene group is selected; more preferably, a $C_1$-$C_6$ alkylene group is selected; furthermore preferably, a $C_2$-$C_4$ alkylene group is selected. Examples of $C_0$-$C_{12}$ alkylene group may specifically include methylene, ethylene, propylene, isopropylidene, butylene, isobutylene, sec-butylene, pentylene, and hexylene.

The $C_2$-$C_{12}$ alkenylene group may be a straight chain alkenylene group or a branched chain alkenylene group, and a number of double bonds in the $C_2$-$C_{12}$ alkenylene group is preferably one. A preferable lower limit of a quantity of carbon atoms in the $C_2$-$C_{12}$ alkenylene group is 2, 3, 4, and 5, and a preferable upper limit is 4, 5, 6, 7, 8, 9, 10, 11, and 12. Preferably, a $C_2$-$C_{10}$ alkenylene group is selected; more preferably, a $C_2$-$C_6$ alkenylene group is selected; furthermore preferably, a $C_2$-$C_4$ alkenylene group is selected. Examples of $C_2$-$C_{12}$ alkenylene group may specifically include: vinylidene, allylene, isopropenylene, butylene group, and pentenylene.

The $C_2$-$C_{12}$ alkynylene group may be a straight-chain alkynylene group or a branched-chain alkynylene group, and a number of triple bonds in the $C_2$-$C_{12}$ alkynylene group is preferably 1. A preferable lower limit of a quantity of carbon atoms in the $C_2$-$C_{12}$ alkynylene group is 2, 3, 4, and 5, and a preferable upper limit is 4, 5, 6, 7, 8, 9, 10, 11, and 12. Preferably, a $C_2$-$C_{10}$ alkynylene group is selected; more preferably, a $C_2$-$C_6$ alkynylene group is selected; still more preferably, a $C_2$-$C_4$ alkynylene group is selected. Examples of the $C_2$-$C_{12}$ alkynylene group may specifically include: ethynylene, propynylene, isopropynylene, and pentynylene.

The halogen atom as the substituent group may be selected from one or more of a fluorine atom, a chlorine atom, and a bromine atom, and is preferably a fluorine atom.

(1) Specifically, the compound represented by the Formula II-1 is an aliphatic dinitrile compound.

In the Formula II-1, preferably, $R_5$ is selected from a substituted or unsubstituted $C_1$-$C_{10}$ alkylene group, a substituted or unsubstituted $C_2$-$C_{10}$ alkenylene group, a substituted or unsubstituted $C_2$-$C_{10}$ alkynylene group; where the substituent group is selected from a halogen atom, preferably a fluorine atom. More preferably, $R_5$ is selected from a $C_1$-$C_6$ alkylene group, a $C_2$-$C_6$ alkenylene group, and a $C_2$-$C_6$ alkynylene group. Furthermore preferably, $R_5$ is selected from a $C_2$-$C_4$ alkylene group, a $C_2$-$C_4$ alkenylene group, and a $C_2$-$C_4$ alkynylene group.

Preferably, the compound represented by the Formula II-1 can be selected from one or more of succinonitrile, glutaronitrile, adiponitrile, pimenonitrile, suberonitrile, azelaonitrile, sebaconitrile, undecane dinitrile, dodecane dinitrile, tetramethyl succinonitrile, methyl glutaronitrile, butenedinitrile, 2-pentene dinitrile, hex-2-ene dionitrile, hex-3-ene dinitrile, oct-4-ene dinitrile and oct-4-yne dinitrile.

More preferably, the compound represented by the Formula II-1 may be selected from one or more of succinonitrile, glutaronitrile, adiponitrile, butenedionitrile, 2-pentene dionitrile, and hexa-3-ene dionitrile, and a specific structure is as follows:

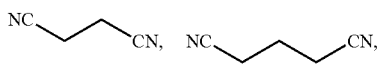

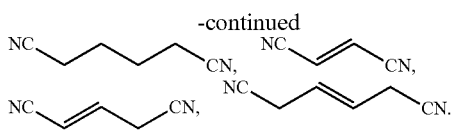

(2) Specifically, the compound represented by the Formula II-2 is an aliphatic polynitrile compound.

In the Formula II-2, preferably, $R_6$, $R_7$, and $R_8$ each are independently selected from a substituted or unsubstituted $C_0$-$C_{10}$ alkylene group, a substituted or unsubstituted a $C_2$-$C_{10}$ alkenylene group, a substituted or unsubstituted $C_2$-$C_{10}$ alkynylene group; where the substituent group is selected from a halogen atom, preferably a fluorine atom. More preferably, $R_6$, $R_7$, and $R_8$ each are independently selected from a $C_0$-$C_6$ alkylene group, a $C_2$-$C_6$ alkenylene group, and a $C_2$-$C_6$ alkynylene group. More preferably, $R_6$ is selected from a $C_0$-$C_1$ alkylene group, and $R_7$ and $R_8$ each are independently selected from a $C_2$-$C_4$ alkylene group, a $C_2$-$C_4$ alkenylene group, and a $C_2$-$C_4$ alkynylene group.

Preferably, the compound represented by the Formula II-2 may be selected from one or more of 1,2,3-propanetricarbonitrile, 1,3,5-pentatricarbonitrile, and 1,3,6-hexanetricarbonitrile, and a specific structure is as follows:

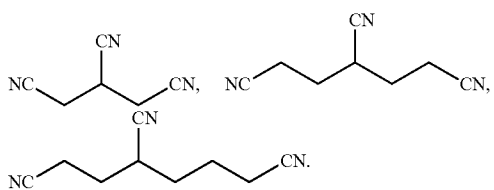

In the lithium-ion battery of the present application, the electrolyte may further contain an additive C. The additive C may be selected from one or more of a cyclic carbonate compound containing a carbon-carbon unsaturated bond, a halogen-substituted cyclic carbonate compound, a sulfate ester compound, a sultone compound, a disulfonate compound, a sulfite compound, an aromatic compound, an isocyanate compound, a phosphazene compound, an acid anhydride compound, a phosphite compound, a phosphate compound, and a borate compound.

Preferably, the mass percentage of the additive C in the electrolyte is 0.01%-30%.

(a) Cyclic Carbonate Compound Containing a Unsaturated Carbon-Carbon Bond

The cyclic carbonate compound containing a carbon-carbon unsaturated bond may be selected from one or more of the compounds represented by Formula III-0. In Formula III-0, $R_{20}$ is selected from a $C_1$-$C_6$ alkylene group substituted with an alkenyl group or an alkynyl group, a substituted or unsubstituted $C_2$-$C_6$ linear alkenylene group, where the substituent group is selected from one or more of a halogen atom, a $C_1$-$C_6$ alkyl group, and a $C_2$-$C_6$ alkenyl group.

Formula III-0

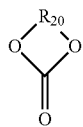

Preferably, the cyclic carbonate compound containing a carbon-carbon unsaturated bond may be specifically selected from one or more of the following compounds, but the present application is not limited thereto:

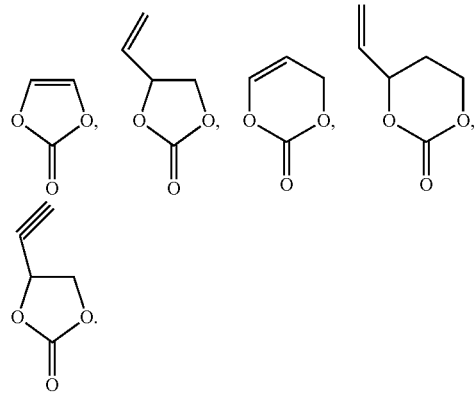

(b) Halogen Substituted Cyclic Carbonate Compound

The halogen-substituted cyclic carbonate compound may be selected from one or more of the compounds represented by Formula III-1. In the Formula III-1, $R_{21}$ is selected from a halogen-substituted $C_1$-$C_6$ alkylene group and a halogen-substituted $C_2$-$C_6$ alkenylene group.

Formula III-1

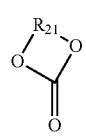

Specifically, the halogen-substituted cyclic carbonate compound may be selected from or one or more of fluoroethylene carbonate (abbreviated as FEC), fluoropropylene carbonate (abbreviated as FPC), trifluoropropylene carbonate (abbreviated as TFPC), trans-4,5-difluoro-1,3-dioxolane-2-one or cis-4,5-difluoro-1,3-dioxolane-2-one (hereinafter the two are collectively referred to as "DFEC").

(c) Sulfate Compound

The sulfate compound is preferably a cyclic sulfate compound, and the cyclic sulfate compound may be selected from one or more of the compounds represented by Formula III-2. In the Formula III-2, $R_{22}$ is selected from a substituted or unsubstituted $C_1$-$C_6$ alkylene group, a substituted or unsubstituted $C_2$-$C_6$ alkenylene group, where the substituent group is selected from one or more of a halogen atom, a $C_1$-$C_3$ alkyl group, or a $C_2$-$C_4$ alkenyl group.

Formula III-2

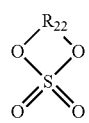

In the Formula III-2, preferably, $R_{22}$ is selected from a substituted or unsubstituted $C_1$-$C_4$ alkylene group, a substituted or unsubstituted $C_2$-$C_4$ alkenylene group, where the substituent group is selected from one or more of a halogen atom, a $C_1$-$C_3$ alkane, and a $C_2$-$C_4$ alkenyl group.

Preferably, the sulfate compound may be specifically selected from one or more of the following compounds, but the present application is not limited to this:

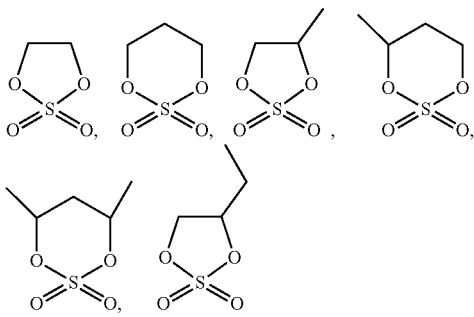

More preferably, the sulfate compound is selected from one or more of ethylene sulfate (abbreviated as DTD), trimethylene sulfite (abbreviated as TMS), and propylene sulfate (abbreviated as PLS), the specific structures thereof are as follows:

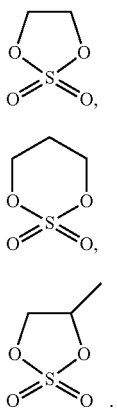

(DTD)

(TMS)

(PLS)

(d) Sultone Compound

The sultone compound may be selected from one or more of the compounds represented by Formula III-3. In Formula III-3, $R_{23}$ is selected from a substituted or unsubstituted $C_1$-$C_6$ alkylene group, a substituted or unsubstituted $C_2$-$C_6$ alkenylene group, where the substituent is selected from one or more of a halogen atom, a $C_1$-$C_3$ alkyl group, and a $C_2$-$C_4$ alkenyl group.

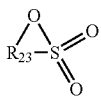

Formula III-3

In Formula III-3, preferably, $R_{23}$ is selected from a substituted or unsubstituted $C_1$-$C_4$ alkylene group, a substituted or unsubstituted $C_2$-$C_4$ alkenylene group, where the substituent group is selected from one or more of a halogen atom, a $C_1$-$C_3$ alkane group and a $C_2$-$C_4$ alkenyl group.

Preferably, the sultone compound may be specifically selected from one or more of the following compounds, but the present application is not limited thereto:

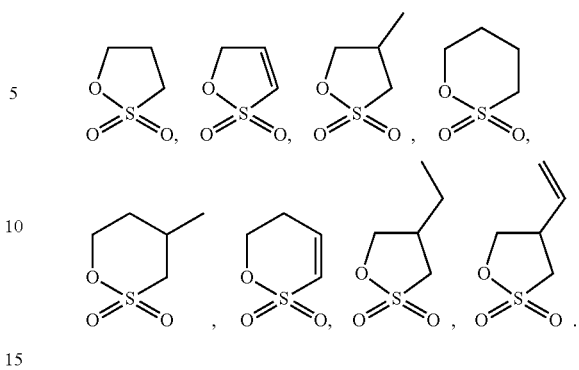

More preferably, the sultone compound may be selected from one or more of 1,3-propane sultone (abbreviated as PS) and 1,3-propene sultone (abbreviated as PES), and the specific structures are as follows:

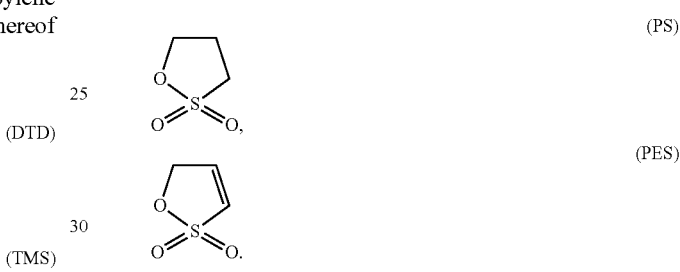

(PS)

(PES)

(e) Disulfonate Compound

The disulfonate compound is a compound containing two sulfonic acid groups (—S(=O)2O—), preferably selected from a methylene disulfonate compound, and the methylene disulfonate compound may be selected from one or more of the compounds represented by Formula III-4. In Formula III-4, $R_{24}$, $R_{25}$, $R_{26}$, and $R_{27}$ each are independently selected from a hydrogen atom, a halogen atom, a substituted or unsubstituted $C_1$-$C_{10}$ alkyl group, a substituted or unsubstituted $C_2$-$C_{10}$ alkenyl group, where the substituent group is selected from one or more of a halogen atom, a $C_1$-$C_3$ alkyl group, and a $C_2$-$C_4$ alkenyl group.

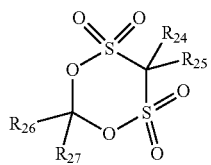

Formula III-4

In Formula III-4, preferably, $R_{24}$, $R_{25}$, $R_{26}$, and $R_{27}$ each are independently selected from a hydrogen atom, a halogen atom, a substituted or unsubstituted $C_1$-$C_4$ alkyl group, and a substituted or unsubstituted $C_2$-$C_6$ alkenyl group, where the substituent group is selected from one or more of a halogen atoms, a $C_1$-$C_3$ alkyl group, and a $C_2$-$C_4$ alkenyl group.

Preferably, the disulfonate compound may be specifically selected from one or more of the following compounds, but the present application is not limited to this:

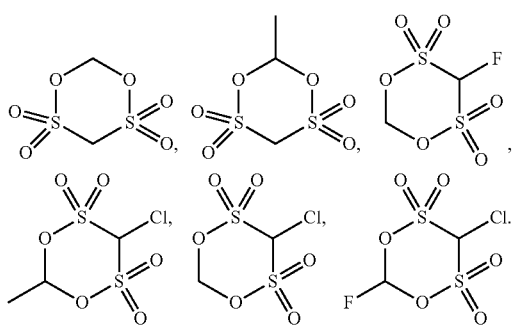

More preferably, the disulfonate compound may be selected from methylene methanedisulfonate (abbreviated as MMDS), and the specific structure is as follows:

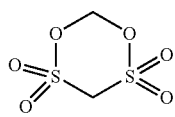

(f) Sulfite Compound

The sulfite compound is preferably a cyclic sulfite compound, which can be specifically selected from one or more of the compounds represented by Formula III-5. In Formula III-5, $R_{28}$ is selected from a substituted or unsubstituted $C_1$-$C_6$ alkylene group, a substituted and a unsubstituted $C_2$-$C_6$ alkenylene group, where the substituent group is selected from one or more of a halogen atom, a $C_1$-$C_3$ alkyl group, a $C_2$-$C_4$ alkenyl group.

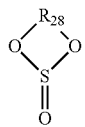

Formula II-5

In Formula III-5, preferably, $R_{28}$ is selected from a substituted or unsubstituted $C_1$-$C_4$ alkylene group, a substituted or unsubstituted $C_2$-$C_4$ alkenylene group, where the substituent group is selected from one or more of a halogen atom, a $C_1$-$C_3$ alkane, and a $C_2$-$C_4$ alkenyl group.

Preferably, the sulfite compound may be selected from one or more of ethylene sulfite (abbreviated as ES), propylene sulfite (abbreviated as PS), and butylene sulfite (abbreviated as BS).

(g) Aromatic Compound

The aromatic compound may be selected from one or more of cyclohexylbenzene, fluorocyclohexylbenzene compounds (1-fluoro-2-cyclohexylbenzene, 1-fluoro-3-cyclohexylbenzene, 1-fluoro-4-cyclohexylbenzene), tert-butylbenzene, tert-amylbenzene, 1-fluoro-4-tert-butylbenzene, biphenyl, terphenyl (ortho, meta, para), diphenyl ether, fluorobenzene, difluorobenzene (ortho, meta, para), anisole, 2,4-difluoroanisole, partially hydrogenated product of terphenyl (1,2-dicyclohexylbenzene, 2-phenylbicyclohexyl, 1,2-diphenylcyclohexane, o-cyclohexylbiphenyl).

Preferably, the aromatic compound may be selected from one or more of biphenyl, terphenyl (ortho, meta, para), fluorobenzene, cyclohexylbenzene, tert-butylbenzene, and tert-amylbenzene. Further preferably, the aromatic compound may be selected from one or more of biphenyl, o-terphenyl, fluorobenzene, cyclohexylbenzene, and tert-amylbenzene.

(h) Isocyanate Compound

The isocyanate compound may be selected from one or more of methyl isocyanate, ethyl isocyanate, butyl isocyanate, phenyl isocyanate, tetramethylene diisocyanate, hexamethylene diisocyanate, octamethylene diisocyanate, 1,4-phenylene diisocyanate, 2-isocyanatoethyl acrylate, and 2-isocyanatoethyl methacrylate.

Preferably, the isocyanate compound may be selected from one or more of hexamethylene diisocyanate, octamethylene diisocyanate, 2-isocyanatoethyl acrylate, and 2-isocyanatoethyl methacrylate.

(i) Phosphononitrile Compound

The phosphazene compound is preferably a cyclic phosphazene compound. The cyclic phosphazene compound may be selected from one or more of methoxy pentafluorocyclotriphosphazene, ethoxy pentafluorocyclotriphosphazene, phenoxy pentafluorocyclotriphosphazene, and ethoxy heptafluorocyclotetraphosphazene.

Preferably, the cyclic phosphazene compound may be selected from one or more of methoxy pentafluorocyclotriphosphazene, ethoxy pentafluorocyclotriphosphazene, and phenoxy pentafluorocyclotriphosphazene.

More preferably, the cyclic phosphazene compound can be selected from methoxy pentafluorocyclotriphosphazene or ethoxy pentafluorocyclotriphosphazene.

(j) Acid Anhydride Compound

The acid anhydride compound may be a chain acid anhydride or a cyclic acid anhydride. Specifically, the acid anhydride compound may be selected from one or more of acetic anhydride, propionic anhydride, succinic anhydride, maleic anhydride, 2-allyl succinic anhydride, glutaric anhydride, itaconic anhydride, and 3-sulfo-propionic anhydride.

Preferably, the acid anhydride compound may be selected from one or more of succinic anhydride, maleic anhydride, and 2-allyl succinic anhydride. More preferably, the acid anhydride compound may be selected from one or both of succinic anhydride and 2-allyl succinic anhydride.

(k) Phosphite Compound

The phosphite compound may be selected from a silane phosphite compound, and specifically may be selected from one or more of the compounds represented by Formula III-6. In the Formula III-6, $R_{31}$, $R_{32}$, $R_{33}$, $R_{34}$, $R_{35}$, $R_{36}$, $R_{37}$, $R_{38}$, and $R_{39}$ each are independently selected from a halogen-substituted or unsubstituted $C_1$-$C_6$ alkyl group.

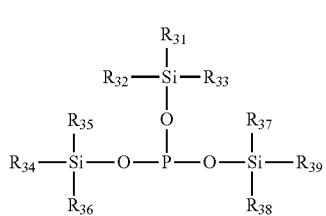

Formula III-6

Preferably, the silane phosphite compound may be specifically selected from one or more of the following compounds, but the present application is not limited thereto:

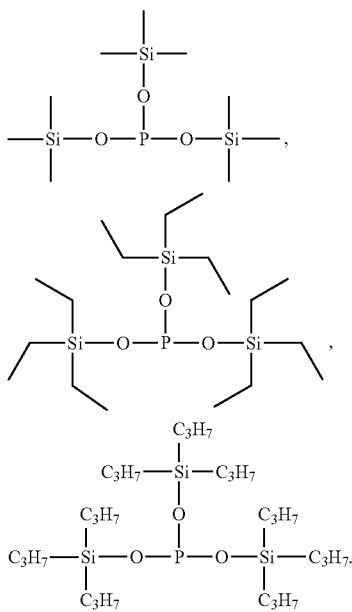

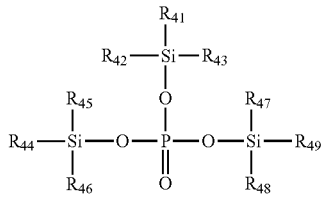

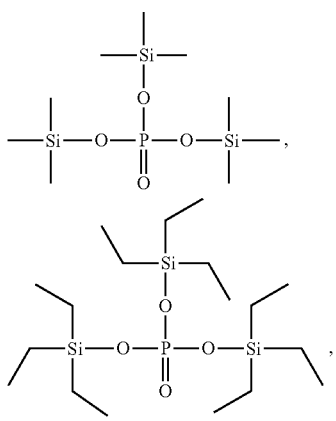

(l) Phosphate Compound

The phosphate compound may be selected from a silane phosphate compound, and specifically may be selected from one or more of the compounds represented by Formula III-7. In the Formula III-7, $R_{41}$, $R_{42}$, $R_{43}$, $R_{44}$, $R_{45}$, $R_{46}$, $R_{47}$, $R_{48}$, and $R_{49}$ each are independently selected from a halogen-substituted or unsubstituted $C_1$-$C_6$ alkyl group.

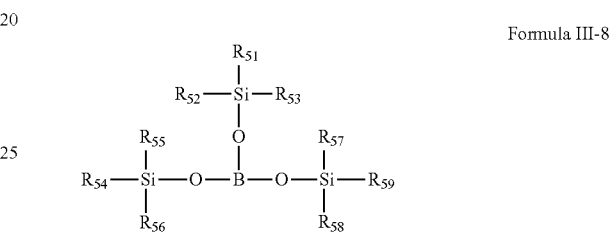

Formula III-7

Preferably, the silane phosphate compound may be specifically selected from one or more of the following compounds, but the present application is not limited thereto:

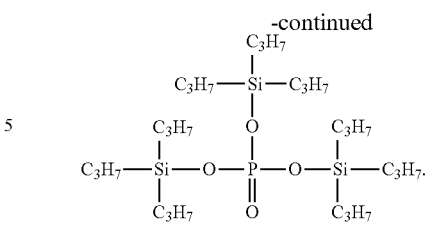

(m) Borate Compound

The borate compound may be selected from a silane borate compound, and specifically may be selected from one or more of the compounds represented by Formula III-8. In Formula III-8, $R_{51}$, $R_{52}$, $R_{53}$, $R_{54}$, $R_{55}$, $R_{56}$, $R_{57}$, $R_{58}$, and $R_{59}$ each are independently selected from a halogen-substituted or unsubstituted $C_1$-$C_6$ alkyl group.

Formula III-8

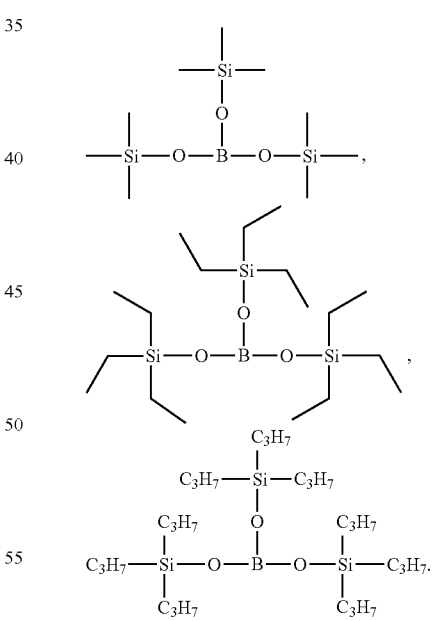

Preferably, the silane borate compound can be specifically selected from one or more of the following compounds, but the present application is not limited thereto:

In the lithium-ion battery of the present application, the electrolyte further includes an organic solvent and an electrolyte salt.

The organic solvent used in the electrolyte of the example of the present application may include a cyclic carbonate and a chain carbonate, which may further improve the cycle performance and storage performance under high-temperature and high-voltage conditions, and which will adjust the conductivity of the electrolyte to an appropriate range. Thus it is more favorable for each additive to achieve a better film-forming effect.

The organic solvent used in the electrolyte of the example of the present application may further include a carboxylic acid ester, that is, the organic solvent according to the present application may include a mixture of cyclic carbonate, chain carbonate, and carboxylic acid ester. Carboxylic acid ester has the characteristics of large dielectric constant and low viscosity, which can effectively prevent the association of ions with anions in the electrolyte, and are more advantageous to and cyclic carbonates and chain carbonates in terms of ion conduction, especially at low temperature, thus the electrolyte can be guaranteed to good ion conductivity.

Based on the total mass of the organic solvent: the mass percentage of the cyclic carbonate may be 15% to 55%, preferably 25% to 50%; the mass percentage of the chain carbonate may be 15% to 74%, preferably 25% to 70%; the mass percentage of the the carboxylic acid ester may be 0.1% to 70%, preferably 5% to 50%.

Specifically, the cyclic carbonate may be selected from one or more of ethylene carbonate, propylene carbonate, 1,2-butene carbonate, and 2,3-butylene glycol carbonate. More preferably, the cyclic carbonate may be selected from one or more of ethylene carbonate and propylene carbonate.

Specifically, the chain carbonate may be an asymmetric chain carbonate selected from one or more of ethyl methyl carbonate, methyl propyl carbonate, methyl isopropyl carbonate, methyl butyl carbonate, and ethylene propyl carbonate; the chain carbonate may also be a symmetric chain carbonate selected from one or more of dimethyl carbonate, diethyl carbonate, dipropyl carbonate, dibutyl carbonate; the chain carbonate may also be a mixture of the abovementioned asymmetric chain carbonate and symmetric chain carbonate.

Specifically, the carboxylic acid ester may be selected from one or more of methyl pivalate, ethyl pivalate, propyl pivalate, butyl pivalate, methyl butyrate, ethyl butyrate, propyl butyrate, butyrate butyl ester, methyl propionate, ethyl propionate, propyl propionate, butyl propionate, methyl acetate, ethyl acetate, propyl acetate, and butyl acetate.

As the electrolyte salt used in the present application, the following lithium salts can be suitably exemplified.

[Li Salt-Type 1]: "a complex salt of Lewis acid with LiF" selected from one or more $LiPF_6$, $LiBF_4$, $LiAsF_6$, $LiSbF_6$, $LiPF_4(CF_3)_2$, $LiPF_3(C_2F_5)_3$, $LiPF_3(CF_3)_3$, $LiPF_3(iso\text{-}C_3F_7)_3$ and $LiPF_5(iso\text{-}C_3F_7)$, where preferably selected from $LiPF_6$, $LiBF_4$, $LiAsF_6$, and more preferably selected from $LiPF_6$, $LiBF_4$, may be suitably exemplified.

[Li Salt-Type 2]: "an imine or methylated lithium salt" selected from one or more of $(CF_2)_2(SO_2)_2NLi$ (cyclic), $(CF_2)_3(SO_2)_2NLi$ (cyclic) and $LiC(SO_2CF_3)_3$ may be suitably exemplified.

[Li Salt-Type 3]: "a lithium salt containing a $S(=O)_2O$ structure" selected from one or more of $LiSO_3F$, $LiCF_3SO_3$, $CH_3SO_4Li$, $C_2H_5SO_4Li$, $C_3H_7SO_4Li$, lithium trifluoro((methylsulfonyl)oxy) borate (LiTFMSB), lithium pentafluoro ((methylsulfonyl)oxy)phosphate (LiPFMSP), where more preferably selected from $LiSO_3F$, $CH_3SO_4Li$, $C_2H_5SO_4Li$ or LiTFMSB, may be suitably exemplified.

[Li Salt-Type 4]: "a lithium salt containing a P=O or Cl=O structure" selected from one or more of $LiPO_2F_2$, $Li_2PO_3F$, and $LiClO_4$, where preferably selected from $LiPO_2F_2$, $Li_2PO_3F$, may be suitably exemplified.

[Li salt-type 5]: "a lithium salt with oxalate ligand as a positive ion" selected from one or more of lithium bis [oxalate-O,O'] borate (LiBOB), lithium difluoro[oxalate-O, O'] borate, lithium difluorobis[oxalate-O,O'] phosphate (LiPFO) and lithium tetrafluoro[oxalate-O,O'] phosphate, where more preferably selected from LiBOB and LiPFO, may be suitably exemplified.

The abovementioned lithium salts can be used individually or in combination. Preferably, the lithium salt is selected from one or more of $LiPF_6$, $LiP_2F_2$, $Li_2PO_3F$, $LiBF_4$, $LiSO_3F$, lithium trifluoro((methylsulfonyl)oxy) borate (LiTFMSB), lithium bis[oxalate-O,O'] borate (LiBOB), lithium difluorobis[oxalate-O,O'] phosphate (LiPFO) and lithium tetrafluoro[oxalate-O,O'] phosphate. More preferably, the lithium salt is selected from one or more of $LiPF_6$, $LiBF_4$, $LiSO_3F$, lithium trifluoro((methylsulfonyl)oxy) borate (LiTFMSB), $LiPO_2F_2$, lithium bis[oxalate-O,O'] borate (LiBOB) and lithium difluorobis[oxalate-O,O'] phosphate (LiPFO). More preferably, the lithium salt is $LiPF_6$.

In the lithium-ion battery of the present application, the preparation method of the electrolyte is not limited, and can be prepared according to a conventional method for preparing an electrolyte.

In the lithium-ion battery of the present application, preferably, the conductivity of the electrolyte at 25° C. is 4 mS/cm to 12 mS/cm.

In the lithium-ion battery of the present application, preferably, $Li_{x1}Co_{y1}M_{1-y1}O_{2-z1}Q_{z1}$ may be specifically selected from one or more of $LiCo_{0.9}Zr_{0.1}O_2$, $LiCo_{0.9}Ti_{0.1}O_2$, $Li_{1.05}Co_{0.8}Mg_{0.2}O_2$, $Li_{1.01}Co_{0.98}Mg_{0.01}Ti_{0.005}Al_{0.005}O_2$, $Li_{1.05}Co_{0.98}Mg_{0.005}Zr_{0.005}Ti_{0.01}O_{1.9}F_{0.1}$, $Li_{1.1}Co_{0.95}Mg_{0.01}Zr_{0.01}Al_{0.03}O_2$, $Li_{1.04}Co_{0.95}Mg_{0.02}Zr_{0.03}O_{1.95}F_{0.05}$, $Li_{1.06}Co_{0.96}Mg_{0.02}Ti_{0.02}O_2$, $Li_{1.08}Co_{0.97}Mg_{0.01}Zr_{0.01}Al_{0.01}O_{1.9}S_{0.1}$, $Li_{1.09}Co_{0.98}Mg_{0.01}Ti_{0.005}Al_{0.005}O_2$, $Li_{1.085}Co_{0.98}Zr_{0.01}Ti_{0.005}Al_{0.005}O_{1.9}Cl_{0.1}$, $Li_{1.03}Co_{0.96}Mg_{0.01}Zr_{0.01}Ti_{0.01}Al_{0.01}O_2$, $Li_{1.04}Co_{0.97}Zr_{0.01}Al_{0.02}O_{1.9}F_{0.1}$, $Li_{1.07}Co_{0.97}Zr_{0.01}Ti_{0.01}Al_{0.01}O_{1.9}S_{0.1}$, $Li_{1.02}Co_{0.96}Mg_{0.02}Zr_{0.015}Ti_{0.005}O_{1.9}S_{0.1}$, $Li_{1.03}Co_{0.98}Ti_{0.01}Al_{0.01}O_{1.9}Cl_{0.1}$, $Li_{1.05}Co_{0.97}Mg_{0.01}Zr_{0.01}Al_{0.01}O_{1.9}Cl_{0.1}$, $Li_{1.04}Co_{0.95}Zr_{0.02}Ti_{0.03}O_{1.9}F_{0.1}$, $Li_{1.09}Co_{0.97}Mg_{0.02}Ti_{0.01}O_{1.95}F_{0.05}$, $Li_{1.03}Co_{0.95}Mg_{0.03}Ti_{0.02}O_{1.9}S_{0.1}$, $Li_{1.04}Co_{0.97}Zr_{0.01}Ti_{0.01}Al_{0.01}O_{1.9}S_{0.1}$.

In the lithium-ion battery of the present application, the positive active material may further include one or more of lithium nickel oxide, lithium manganese oxide, lithium nickel manganese oxide, lithium nickel cobalt manganese oxide, lithium nickel cobalt aluminum oxide, and a compound obtained by adding one or more of other transition metals or non-transition metals to the aforementioned oxides.

In the lithium-ion battery of the present application, the positive electrode sheet further includes a binder and a conductive agent, and a positive slurry containing the positive active material, the binder and the conductive agent is coated on a positive current collector, and then dried to obtain the positive electrode sheet. Type and content of the conductive agent and the binder are not specifically limited, and may be selected according to actual needs. The type of the positive current collector is also not specifically limited, and can be selected according to actual needs, and is preferably an aluminum foil.

In the lithium-ion battery of the present application, the negative active material in the negative electrode sheet includes one or more of soft carbon, hard carbon, artificial graphite, natural graphite, Si, $SiO_2$, Si/C composite material, Si alloy, lithium titanate, and metal capable of forming an alloy with lithium, wherein $0 < x2 \leq 2$.

In the lithium-ion battery of the present application, the negative electrode sheet further includes a binder and a conductive agent, and a negative slurry containing the negative active material, the binder and the conductive agent is coated on the negative current collector, and then dried to obtain the negative electrode sheet. Type and content of the conductive agent and the binder are not specifically limited, and may be selected according to actual needs. Type of the negative current collector is also not specifically limited, and can be selected according to actual needs, and is preferably a copper foil.

In the lithium-ion battery of the present application, the separation film is disposed between the positive electrode sheet and the negative electrode sheet to play a role of isolation. The specific type of the separation film is specifically limited, and may be any material of a separation film used in existing lithium-ion batteries, such as polyethylene, polypropylene, polyvinylidene fluoride and their multilayer composite film, but not limited to these.

In the lithium-ion battery of the present application, a charge cut-off voltage of the lithium-ion battery is not less than 4.2V, that is, the lithium-ion battery may be used in a high voltage state of not less than 4.2V. Preferably, the charge cut-off voltage of the lithium-ion battery is not less than 4.35V.

The lithium-ion battery of the present application may be either a hard-shell lithium-ion battery or a soft-packaged lithium-ion battery. The hard shell lithium-ion battery preferably uses a hard shell of metal. The soft-packaged lithium-ion battery preferably uses a packaging bag as a battery housing, the packaging bag usually includes an accommodating part and a sealing part, where the accommodating part is used to accommodate the electrode assembly and the electrolyte, and the sealing part is used to seal the electrode assembly and the electrolyte. The electrolyte of the present application improves the performance of soft-packaged lithium-ion batteries more obviously, because soft-packaged lithium-ion batteries are prone to swelling during use, and the electrolyte of the present application may greatly reduce the gas production of the battery, and avoid shortening life caused by the swelling of the soft-packaged lithium-ion batteries.

In the lithium-ion battery of the present application, the additive A may be synthesized by the following method.

(1) Preparation of the Compound Represented by the Formula I-1

A reaction scheme is as follows:

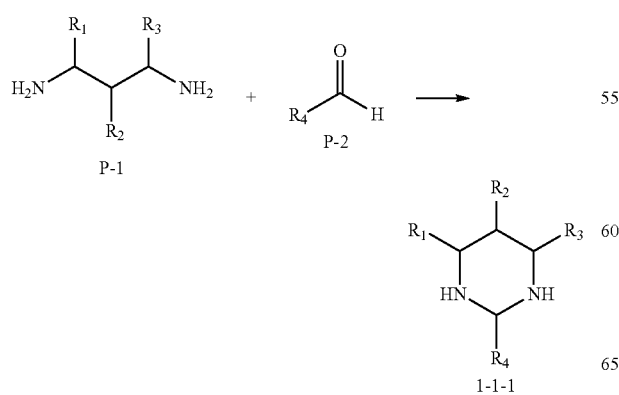

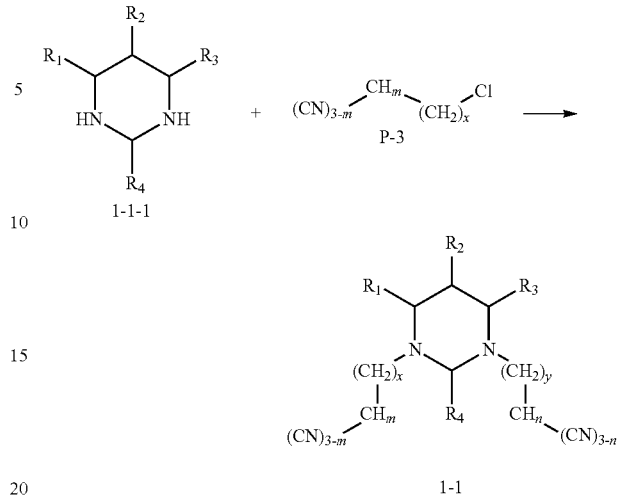

A specific preparation process includes:

adding aqueous solution P-2 with a concentration of 30%-40% dropwise to a raw material P-1 within 20 min 60 min with quickly stirring the solution. After the dropwise addition is completed, quickly stirring the solution for 15 h-30 h. Stirring the solution in an oil bath at 70° C.-90° C. under reflux for 3 h-5 h to obtain a colorless, fuming and viscous liquid intermediate product I-1-1. Then adding $K_2CO_3$, KI, and anhydrous acetonitrile, and quickly stirring them to form a solid-liquid mixture. Quickly adding a raw material P-3 at 40° C.-60° C., then stirring them for 10 h-20 h, and cooling the mixture to room temperature. Then performing separation and purification to obtain the compound represented by the Formula I-1.

(2) Preparation of the Compound Represented by the Formula I-2

A reaction scheme is as follows:

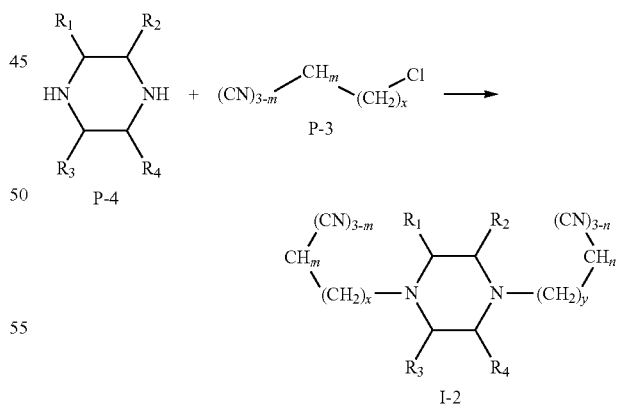

A specific preparation process includes:

mixing anhydrous sodium carbonate, a raw material P-4 and a raw material P-3 in absolute ethanol, and stirring for 2 h-5 h for a reaction; repeatedly washing with hot ethanol for a plurality of times to obtain a crude product, and performing recrystallization to obtain the compound represented by the Formula I-2.

(3) Preparation of the Compound Represented by the Formula I-3

A reaction scheme is as follows:

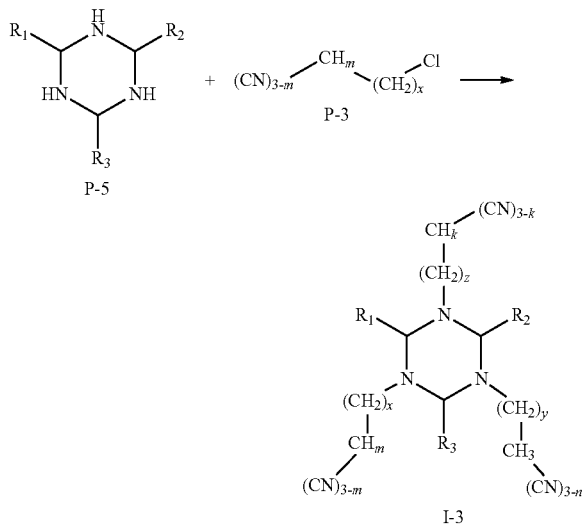

A specific preparation process includes:

mixing anhydrous sodium carbonate, a raw material P-5 and a raw material P-3 in anhydrous ethanol, and stirring for 2 h-5 h for a reaction; repeatedly washing with hot ethanol for a plurality of times to obtain a crude product, and performing recrystallization to obtain the compound represented by the Formula I-3.

In some examples, the lithium-ion battery may include an outer package for encapsulating the positive electrode sheet, the negative electrode sheet, and the electrolyzable substance. As an example, the positive electrode sheet, the negative electrode sheet and the separation film may be laminated or wound to form an electrode assembly of a laminated structure or an electrode assembly of a wound structure, the electrode assembly is encapsulated in an outer package; the electrolyzable substance may be an electrolyte, which infiltrates in the electrode assembly. There may be one or more electrode assemblies in the lithium-ion battery, depending on needs.

In some examples, the outer package of the lithium-ion battery may be a soft package, for example, a soft bag. A material of the soft package may be plastic, for example, may include one or more of polypropylene PP, polybutylene terephthalate PBT, polybutylene succinate PBS, and the like. Alternatively, the outer package of the lithium-ion battery may be a hard shell, for example, an aluminum shell.

Figure 4:
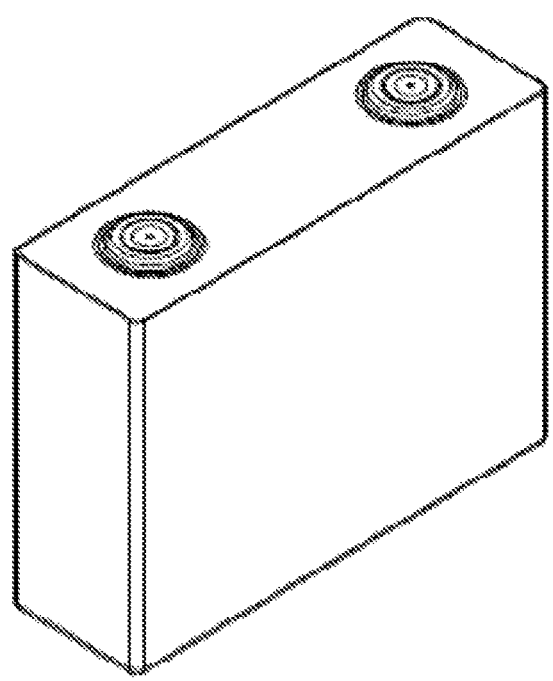
FIG. 4 is a schematic diagram of an embodiment of a lithium-ion battery.

Shape of the lithium-ion battery in the present application is not particularly limited, and may be of a cylindrical, square, or any other shape. FIG. 4 shows an example of a lithium-ion battery 5 of a square structure.

In some Examples, lithium-ion batteries may be assembled into a battery module, and the battery module may include a plurality of lithium-ion batteries, and a specific quantity may be adjusted according to application and capacity of the battery module.

Figure 5:
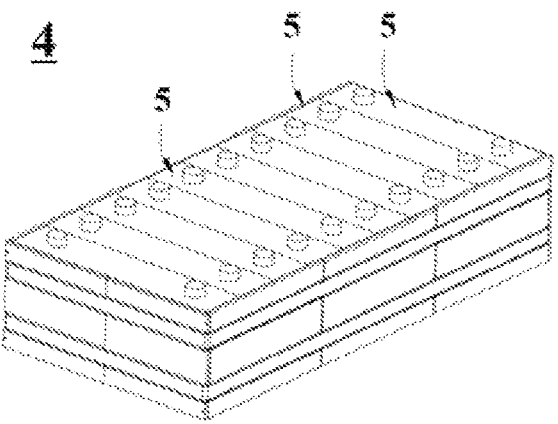
FIG. 5 is a schematic diagram of an embodiment of a battery module.

FIG. 5 shows as an example of a battery module 4. Referring to FIG. 5, in the battery module 4, a plurality of lithium-ion batteries 5 may be sequentially arranged along a length direction of the battery module 4; or certainly, may be arranged in any other manner. Furthermore, the plurality of lithium-ion batteries 5 may be fixed by using fasteners.

Optionally, the battery module 4 may further include a housing with an accommodating space, and the plurality of lithium-ion batteries 5 are accommodated in the accommodating space.

In some Examples, the above-mentioned battery modules can also be assembled into a battery pack, and the quantity of battery modules included in the battery pack can be adjusted according to application and capacity of the battery pack.

Figure 6:
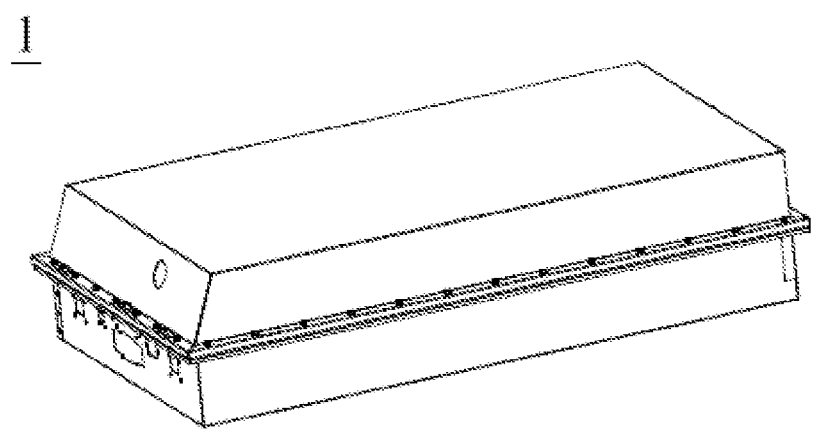
FIG. 6 is a schematic diagram of an embodiment of a battery pack.
Figure 7:
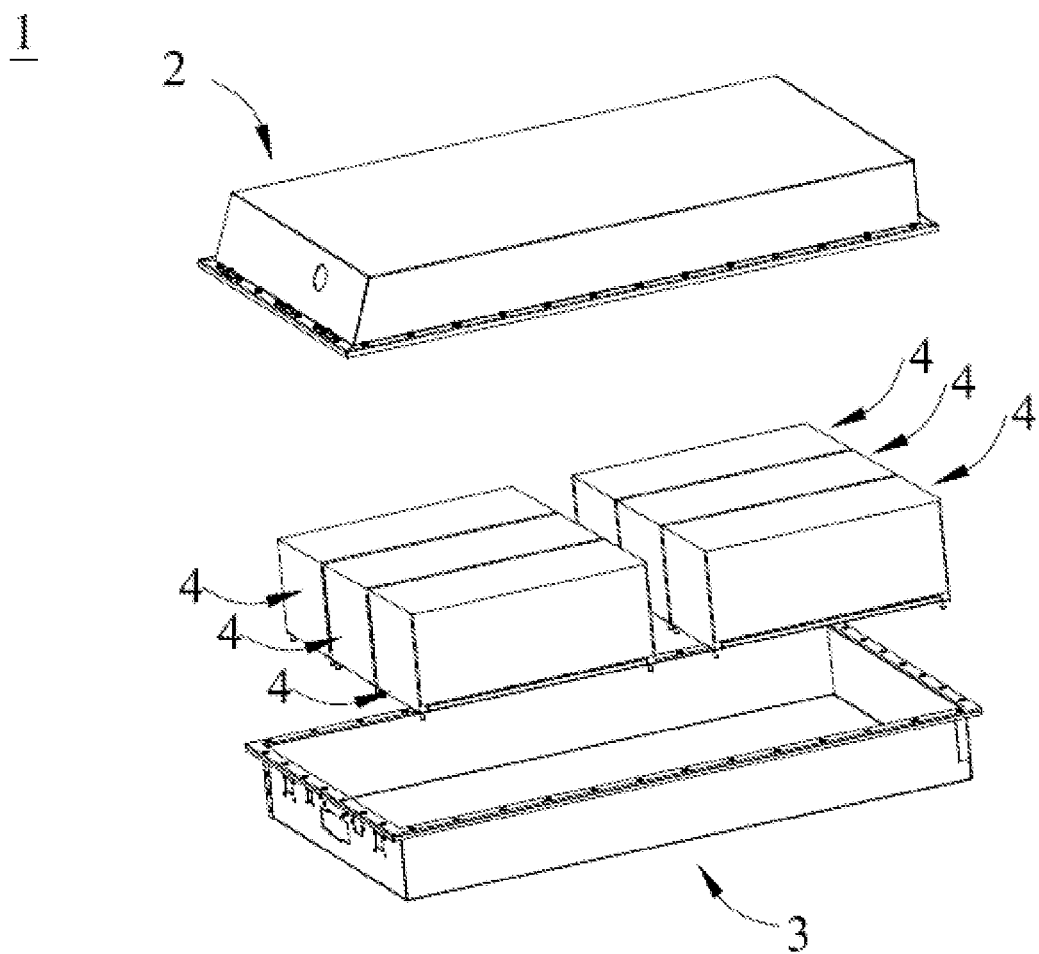
FIG. 7 is an exploded diagram of FIG. 6.

FIG. 6 and FIG. 7 show an example of a battery pack 1. Referring to FIG. 6 and FIG. 7, the battery pack 1 may include a battery cabinet and a plurality of battery modules 4 disposed in the battery cabinet. The battery cabinet includes an upper cabinet body 2 and a lower cabinet body 3. The upper cabinet body 2 can cover the lower cabinet body 3 and form an enclosed space for accommodating the battery module 4. The plurality of battery modules 4 may be arranged in the battery cabinet in any manner.

An apparatus according to a second aspect of the present application will be described next.

In a second aspect of the present application, an apparatus is provided. The apparatus includes the lithium-ion battery in the first aspect of the present application, and the lithium-ion battery supplies power to the apparatus. The apparatus may be, but is not limited to, a mobile device (for example, a mobile phone or a notebook computer), an electric vehicle (for example, a full electric vehicle, a hybrid electric vehicle, a plug-in hybrid electric vehicle, an electric bicycle, an electric scooter, an electric golf vehicle, or an electric truck), an electric train, a ship and a satellite, an energy storage systems, and the like.

A lithium-ion battery, a battery module, or a battery pack may be selected for the apparatus according to requirements for using the apparatus.

Figure 8:
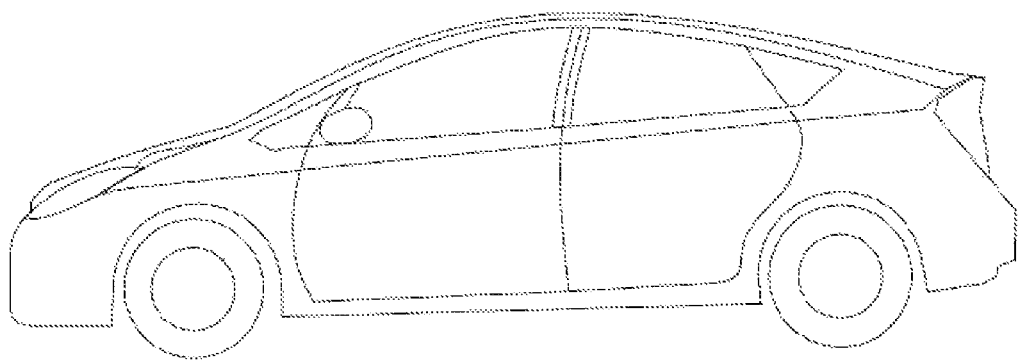
FIG. 8 is a schematic diagram of an embodiment of an apparatus using a lithium-ion battery as a power source.

FIG. 8 shows an example of apparatus. The apparatus is a full electric vehicle, a hybrid electric vehicle, or a plug-in hybrid electric vehicle, or the like. In order to meet a requirement of the apparatus for high power and high energy density of a lithium-ion battery, a battery pack or a battery module may be used.

As another example, the apparatus may be a mobile phone, a tablet computer, a notebook computer, or the like. The apparatus is generally required to be light and thin, and may use a lithium-ion battery as its power source.

To make the purpose, technical solutions, and beneficial technical effects of the present application clearer, the present application will be further described below in detail with reference to Examples. It should be understood that the Examples described in this specification are merely intended to explain the present application, but not to limit the present application. Formulations, proportions, and the like of the examples may be adjusted according to local conditions without substantial effect on results.

All reagents, materials, and instruments that are used in Examples and Comparative Examples are commercially available unless otherwise specified. Specific synthesis processes of additives A1, A2, and A3 are as follows, and other types of additives A may be synthesized according to similar methods.

Synthesis of the Additive A1:

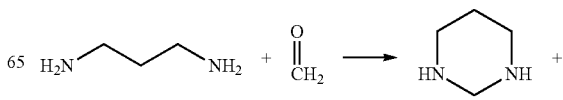

-continued

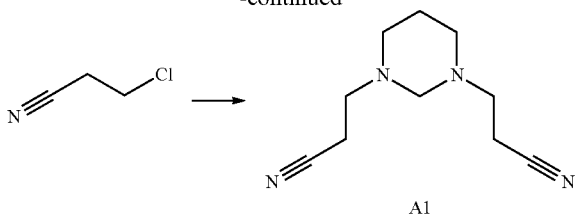

A1

37% formaldehyde aqueous solution is added dropwise to 1,3-propanediamine within 0.5 h with quick stirring. After the dropwise addition is completed, the solution was still quickly stirred for 20 h. Then the solution was stirred in an oil bath at 80° C. reflux for 4 h to obtain intermediate product hexahydropyrimidine as a colorless, fuming, and viscous liquid. $K_2CO_3$, KI, and anhydrous acetonitrile were added, followed by quick stirring to form a solid-liquid mixture. Then P-chloropropionitrile was added at 60° C. within 0.5 h. The mixture was stirred for 17 h, and cooled to room temperature. Then the mixture was subjected to separation and purification to obtain A1. Carbon nuclear magnetic resonance spectrum was shown in FIG. 1.

Synthesis of the Additive A2:

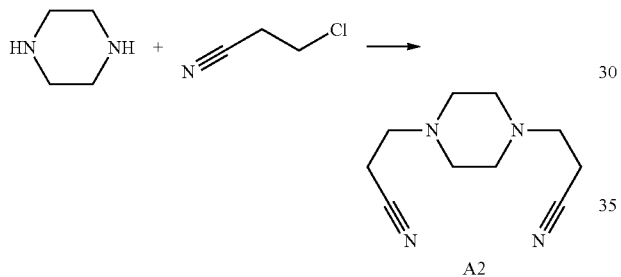

A2

Figure 2:
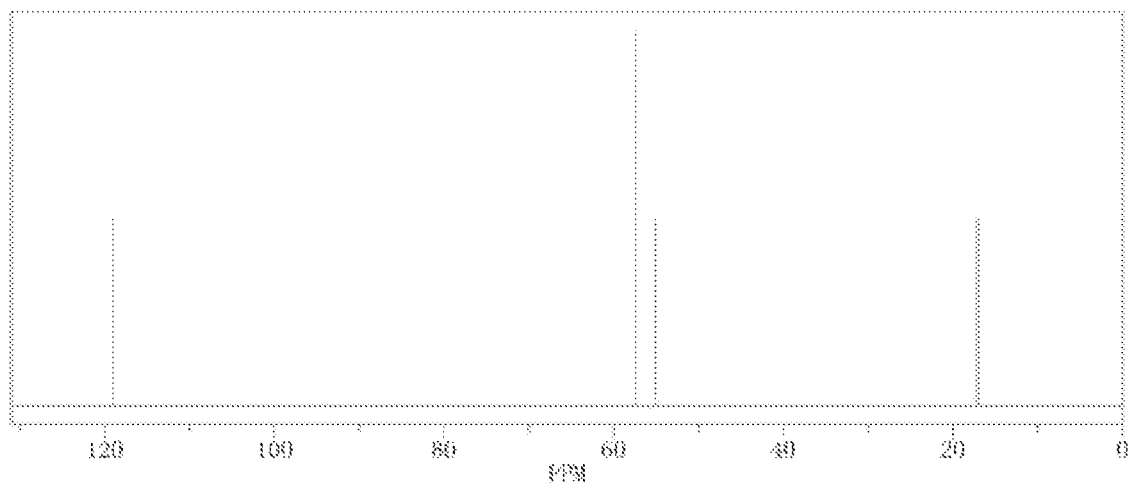
FIG. 2 is a carbon nuclear magnetic resonance spectrum of a compound A2.

Anhydrous sodium carbonate, piperazine and O-chloropropionitrile are mixed in absolute ethanol, and stirred for 4 hours for reaction. The mixture was repeatedly washed with hot ethanol for a plurality of times to obtain a crude product, and subjected to recrystallization to obtain A2. Carbon nuclear magnetic resonance spectrum was shown in FIG. 2.

Synthesis of the Additive A3:

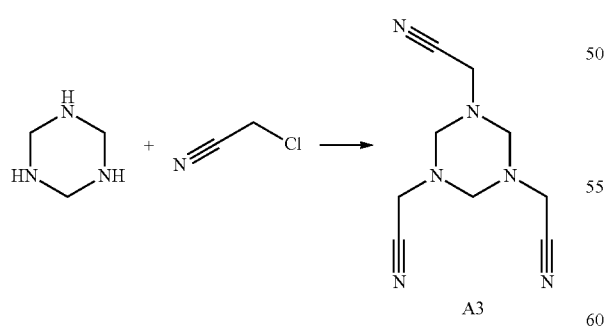

A3

Figure 3:
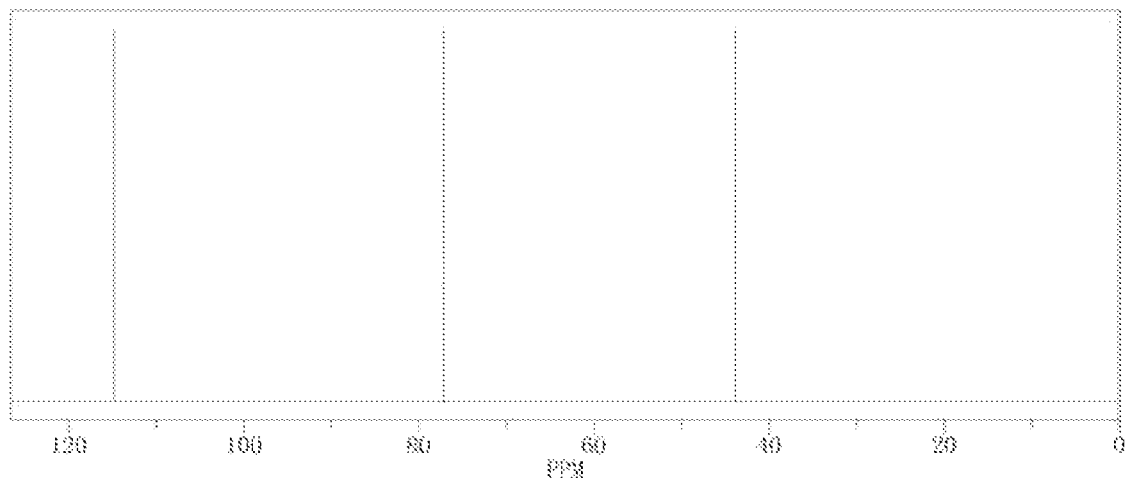
FIG. 3 is a carbon nuclear magnetic resonance spectrum of a compound A3.

Anhydrous sodium carbonate, 1,3,5-s-triazine and chloroacetonitrile were mixed in absolute ethanol, and stirred for 4 h for reaction. The mixture was repeatedly washed with hot ethanol for a plurality of times to obtain a crude product, and subjected to recrystallization to obtain A3. Carbon nuclear magnetic resonance spectrum is shown in FIG. 3.

In Examples 1-24 and Comparative Example 1-2, lithium-ion batteries were prepared according to the following method.

(1) Preparation of an Electrolyte

A mixed solution of ethylene carbonate (EC for short), ethyl methyl carbonate (EMC for short) and diethyl carbonate (DEC for short) was used as an organic solvent, where a mass ratio of EC, EMC and DEC was 1:1:1. $LiPF_6$, was used as a lithium salt in an amount of 12.5% relative to the total mass of the electrolyte. Additives were added according to electrolyte composition as shown in Table 1, where the content of each additive component was calculated relative to the total mass of the electrolyte.

The additives A and B used in the Examples and Comparative Examples are abbreviated as follows:

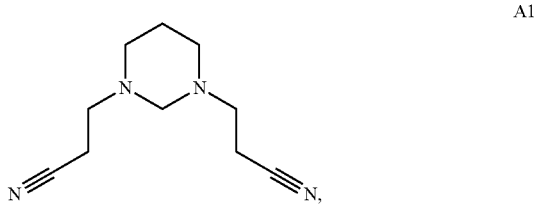
A1

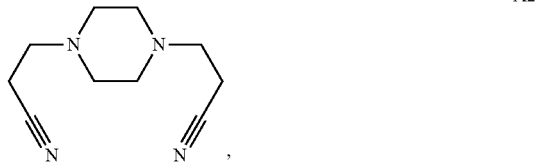
A2

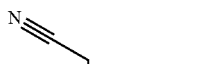
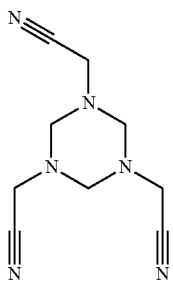
A3

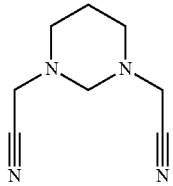
A4

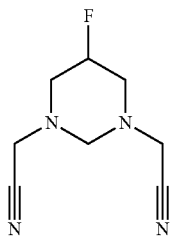
A5

-continued

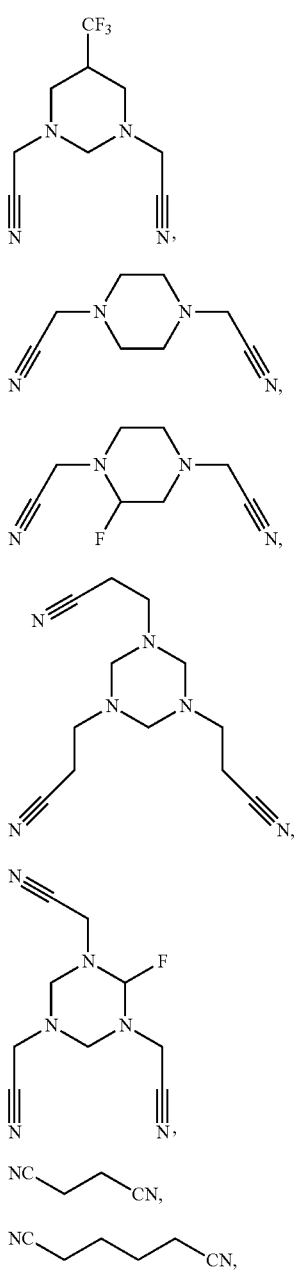

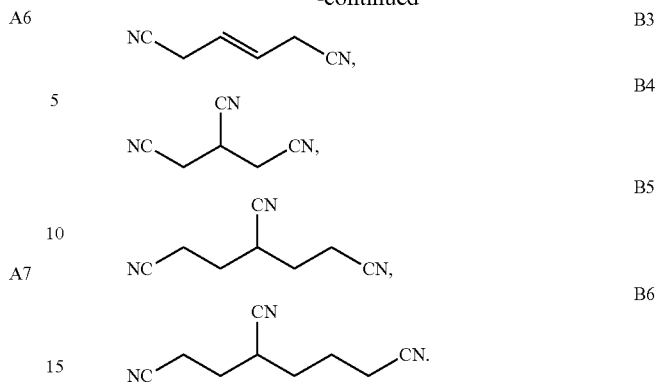

(2) Preparation of a Positive Electrode Sheet

A positive active material, a binder PVDF, and a conductive agent acetylene black shown in Table 1 were mixed at a mass ratio of 98:1:1. N-methylpyrrolidone was added. The resulting mixture was stirred by using a vacuum mixer until the mixture was stable and uniform, to obtain a positive slurry. The positive slurry was uniformly coated onto an aluminum foil. The aluminum foil was dried at room temperature, and transferred to a blast oven at 120° C. to dry for 1 h. Then the aluminum foil was cold-pressed and cut to obtain a positive electrode sheet.

(3) Preparation of a Negative Electrode Sheet

A negative active material graphite, a conductive agent acetylene black, a thickening sodium carboxymethyl cellulose solution, and a binder styrene-butadiene rubber emulsion were mixed at a mass ratio of 97:1:1:1. Deionized water was added. The resulting mixture was stirred by using a vacuum mixer until the mixture was stable and uniform, to obtain a negative slurry. The negative slurry was uniformly coated onto a copper foil. The copper foil was dried at room temperature, and transferred to a blast oven at 120° C. for 1 h. Then the copper foil was cold-pressed and cut to obtain a negative electrode sheet.

(4) Preparation of a Lithium-Ion Battery

The positive electrode sheet, the negative electrode sheet and a PP/PE/PP separation film were wound to obtain the electrode assembly, the electrode assembly was placed into an aluminum plastic film of a packaging bag, followed by injection of the electrolyte, and then a procedure including sealing, standing, hot-pressing and cold-pressing, forming, gas exhausting, and capacity testing were performed to obtain a lithium-ion battery.

TABLE 1

Parameters of Examples 1-24 and Comparative Examples 1-2

| | | Additive A | | Additive B | | Additive C | |
|---|---|---|---|---|---|---|---|
| | Positive active material | Type | Amount | Type | Amount | Type | Amount |
| Example 1 | $Li_{1.05}Co_{0.98}Mg_{0.005}Zr_{0.005}Ti_{0.01}O_{1.9}F_{0.1}$ | A1 | 0.1% | B1 | 2.0% | / | / |
| Example 2 | $Li_{1.05}Co_{0.98}Mg_{0.005}Zr_{0.005}Ti_{0.01}O_{1.9}F_{0.1}$ | A1 | 1.0% | B1 | 2.0% | / | / |
| Example 3 | $Li_{1.05}Co_{0.98}Mg_{0.005}Zr_{0.005}Ti_{0.01}O_{1.9}F_{0.1}$ | A1 | 2.0% | B1 | 2.0% | / | / |
| Example 4 | $Li_{1.05}Co_{0.98}Mg_{0.005}Zr_{0.005}Ti_{0.01}O_{1.9}F_{0.1}$ | A1 | 3.5% | B1 | 2.0% | / | / |
| Example 5 | $Li_{1.05}Co_{0.98}Mg_{0.005}Zr_{0.005}Ti_{0.01}O_{1.9}F_{0.1}$ | A1 | 6.0% | B1 | 2.0% | / | / |
| Example 6 | $Li_{1.05}Co_{0.98}Mg_{0.005}Zr_{0.005}Ti_{0.01}O_{1.9}F_{0.1}$ | A1 | 8.0% | B1 | 2.0% | / | / |
| Example 7 | $Li_{1.05}Co_{0.98}Mg_{0.005}Zr_{0.005}Ti_{0.01}O_{1.9}F_{0.1}$ | A1 | 10.0% | B1 | 2.0% | / | / |
| Example 8 | $Li_{1.05}Co_{0.98}Mg_{0.005}Zr_{0.005}Ti_{0.01}O_{1.9}F_{0.1}$ | A2 | 2.0% | B6 | 0.1% | / | / |
| Example 9 | $Li_{1.05}Co_{0.98}Mg_{0.005}Zr_{0.005}Ti_{0.01}O_{1.9}F_{0.1}$ | A2 | 2.0% | B6 | 0.5% | / | / |
| Example 10 | $Li_{1.05}Co_{0.98}Mg_{0.005}Zr_{0.005}Ti_{0.01}O_{1.9}F_{0.1}$ | A2 | 2.0% | B6 | 1.0% | / | / |

TABLE 1-continued

Parameters of Examples 1-24 and Comparative Examples 1-2

| | Positive active material | Additive A Type | Additive A Amount | Additive B Type | Additive B Amount | Additive C Type | Additive C Amount |
|---|---|---|---|---|---|---|---|
| Example 11 | $Li_{1.05}Co_{0.98}Mg_{0.005}Zr_{0.005}Ti_{0.01}O_{1.9}F_{0.1}$ | A2 | 2.0% | B6 | 3.0% | / | / |
| Example 12 | $Li_{1.05}Co_{0.98}Mg_{0.005}Zr_{0.005}Ti_{0.01}O_{1.9}F_{0.1}$ | A2 | 2.0% | B6 | 5.0% | / | / |
| Example 13 | $Li_{1.05}Co_{0.98}Mg_{0.005}Zr_{0.005}Ti_{0.01}O_{1.9}F_{0.1}$ | A2 | 2.0% | B6 | 8.0% | / | / |
| Example 14 | $Li_{1.05}Co_{0.98}Mg_{0.005}Zr_{0.005}Ti_{0.01}O_{1.9}F_{0.1}$ | A2 | 2.0% | B6 | 10% | / | / |
| Example 15 | $Li_{1.05}Co_{0.98}Mg_{0.005}Zr_{0.005}Ti_{0.01}O_{1.9}F_{0.1}$ | A1 | 2.0% | B1 | 2.0% | EEC | 2.0% |
| Example 16 | $Li_{1.05}Co_{0.98}Mg_{0.005}Zr_{0.005}Ti_{0.01}O_{1.9}F_{0.1}$ | A1 | 2.0% | B1 | 2.0% | DTD | 2.0% |
| Example 17 | $Li_{1.1}Co_{0.95}Mg_{0.01}Zr_{0.01}Al_{0.03}O_2$ | A3 | 2.0% | B2 | 2.0% | / | / |
| Example 18 | $Li_{1.04}Co_{0.95}Mg_{0.02}Zr_{0.03}O_{1.95}F_{0.05}$ | A4 | 2.0% | B2 | 2.0% | / | / |
| Example 19 | $Li_{1.08}Co_{0.97}Mg_{0.01}Zr_{0.01}Al_{0.01}O_{1.9}S_{0.1}$ | A5 | 2.0% | B3 | 2.0% | / | / |
| Example 20 | $Li_{1.085}Co_{0.98}Zr_{0.01}Ti_{0.005}Al_{0.005}O_{1.9}Cl_{0.1}$ | A6 | 2.0% | B3 | 2.0% | / | / |
| Example 21 | $Li_{1.03}Co_{0.96}Mg_{0.01}Zr_{0.01}Ti_{0.01}Al_{0.01}O_2$ | A7 | 2.0% | B4 | 2.0% | / | / |
| Example 22 | $Li_{1.06}Co_{0.96}Mg_{0.02}Ti_{0.02}O_2$ | A8 | 2.0% | B4 | 2.0% | / | / |
| Example 23 | $Li_{1.09}Co_{0.98}Mg_{0.01}Ti_{0.005}O_2$ | A9 | 2.0% | B5 | 2.0% | / | / |
| Example 24 | $Li_{1.04}Co_{0.97}Zr_{0.01}Al_{0.02}O_{1.9}F_{0.1}$ | A10 | 2.0% | B5 | 2.0% | / | / |
| Comparative Example 1 | $LiCoO_2$ | / | / | / | / | / | / |
| Comparative Example 2 | $LiCoO_2$ | / | / | B1 | 2.0% | / | / |

Tests for lithium-ion batteries are described below.

(1) Cyclic Performance Test for a Lithium-Ion Battery at Normal Temperature and High Voltage At 25° C., the lithium-ion battery is charged at a constant current of 1 C until a voltage of 4.35 V is reached, further charged at a constant voltage of 4.35 V until a current of 0.05 C is reached, and then discharged at a constant current of 1 C until a voltage of 3.0 V is reached. This is a charge/discharge cycle process, and the obtained discharge capacity at this time is the discharge capacity at the first cycle. A lithium-ion battery is subjected to charge/discharge test according to the foregoing method for 200 cycles, to determine a discharge capacity at the 200$^{th}$ cycle.

Capacity retention rate (%) of the lithium-ion battery after 200 cycles=(the discharge capacity of the lithium-ion battery after 200 cycles/the discharge capacity of the lithium-ion battery at the first cycle)×100%.

(2) Cyclic Performance Test for a Lithium-Ion Battery Under High-Temperature and High-Voltage Conditions At 45° C., the lithium-ion battery is charged at a constant current of 1 C until a voltage of 4.35 V is reached, further charged at a constant voltage of 4.35 V until a current of 0.05 C is reached, and then discharged at a constant current of 1 C until a voltage of 3.0 V is reached. This is a charge/discharge cycle process, and the obtained discharge capacity at this time is the discharge capacity at the first cycle. A lithium-ion battery is subjected to charge/discharge test according to the foregoing method for 200 cycles, to determine a discharge capacity at the 200$^{th}$ cycle.

Capacity retention rate (%) of a lithium-ion battery after 200 cycles=(the discharge capacity of the lithium-ion battery after 200 cycles/the discharge capacity of the lithium-ion battery at the first cycle)×100%.

(3) Storage Performance Test for a Lithium-Ion Battery at a High Temperature

At 25° C. the lithium-ion battery is charged at a constant current of 0.5 C until a voltage of 4.35 V is reached, and then charged at a constant voltage of 4.35 V until a current of 0.05 C is reached. The thickness of the lithium-ion battery is tested and denoted the thickness as $h_0$. Then the lithium-ion battery is placed in a constant-temperature box at 85° C., stored for 24 h, and then taken out. Then the thickness of the lithium-ion battery is tested again and denoted as $h_1$.

Thickness expansion rate (%) of the lithium-ion battery after storage at 85° C. for 24 h=$[(h_1-h_0)/h_0]\times100\%$.

TABLE 2

Performance test results of Examples 1-24 and Comparative Examples 1-2

| | Capacity retention rate after 200 cycles at 25° C./4.35 V | Capacity retention rate after 200 cycles at 45° C./4.35 V | Thickness expansion rate at 85° C./24 h |
|---|---|---|---|
| Example 1 | 91% | 88% | 15% |
| Example 2 | 94% | 90% | 9% |
| Example 3 | 98% | 94% | 4% |
| Example 4 | 96% | 92% | 3% |
| Example 5 | 93% | 87% | 2% |
| Example 6 | 88% | 80% | 2% |
| Example 7 | 82% | 74% | 1% |
| Example 8 | 96% | 91% | 8% |
| Example 9 | 98% | 93% | 6% |
| Example 10 | 98% | 94% | 5% |
| Example 11 | 96% | 92% | 4% |
| Example 12 | 92% | 88% | 2% |
| Example 13 | 84% | 77% | 1% |
| Example 14 | 78% | 69% | 1% |
| Example 15 | 99% | 96% | 4% |
| Example 16 | 98% | 95% | 2% |
| Example 17 | 97% | 93% | 5% |
| Example 18 | 96% | 92% | 4% |
| Example 19 | 98% | 94% | 6% |
| Example 20 | 95% | 91% | 3% |
| Example 21 | 96% | 92% | 5% |
| Example 22 | 98% | 94% | 3% |
| Example 23 | 97% | 93% | 4% |
| Example 24 | 96% | 92% | 4% |
| Comparative Example 1 | 85% | 78% | 42% |
| Comparative Example 2 | 89% | 85% | 18% |

It can be seen from comparisons between Examples 1-24 and Comparative Examples 1-2 that lithium-ion batteries of the present application have super cycle performance and storage performance under high-temperature and high-voltage conditions.

Compared with Comparative Example 1, in Examples of the present application, the metal ion M-doped lithium cobalt oxide material $Li_{x1}Co_{y1}M_{1-y1}O_{2-z1}Q_{z1}$ was used as the positive active material, and the combined additive of additive A and additive B was used as an electrolyte additive. The doping element M served as a framework in the positive active material, which can reduce lattice deformation during deep delithiation process of the positive active material, delay degradation of bulk structure of the positive active material, and greatly improve structural stability of the lithium-ion battery when the lithium-ion battery was used under high-voltage conditions. The additive A was a polynitrile six-membered nitrogen-heterocyclic compound with a relatively low oxidation potential, such that a stable complex layer was formed on a surface of the positive active material during formation of the battery, which effectively passivated the surface of the positive active material, reduced surface activity of the positive active material, and avoided direct contact between the electrolyte and the surface of the positive active material, thereby greatly reducing surface side reactions, and correspondingly reducing lithium ions consumed in the side reactions, and thus greatly decreasing a consumption rate of reversible lithium ions. The actual effect finally manifested was that capacity retention rate of the lithium-ion battery after cycling was greatly increased. Due to the production gas in some surface side reactions, the reduction of surface side reactions further indicated a decrease in gas production of the battery. The actual effect finally manifested was that thickness expansion of the lithium-ion battery was significantly reduced at high temperature. The additive B was an aliphatic dinitrile or polynitrile compound with a higher oxidation potential, which can stably exist in the electrolyte for a long time and can repair the damaged complex layer (formed by the additive A) at any time during cycling or high temperature storage, reduce the dissolution of transition metal ions, and greatly reduce the damage of the transition metal to the SEI film deposited on the negative electrode after the dissolution of the transition metal. Therefore, the present application can significantly improve the cycle performance and storage performance of lithium-ion batteries under high-temperature and high-voltage conditions.

Compared with the linear nitrile compound used in Comparative Example 2, the polynitrile six-membered nitrogen-heterocyclic compound of the present application has a special six-membered nitrogen-heterocyclic structure with a spacing between nitrile groups closer to that between transition metals on the surface of the positive active material. This can maximize complexation of the nitrile group and allow more nitrile groups to have a complexation effect. Therefore, the polynitrile six-membered nitrogen-heterocyclic compound of the present application had stronger coverage on a transition metal on the surface of the positive active material, better passivation effect on the surface of the positive active material, and also outstanding improvement on cycle performance and storage performance of the lithium-ion battery.

It can be further seen from Examples 1-7 that, when an end-of-charge voltage was fixed at 4.35 V, with an increase (from 0.1% to 10%) in the amount of the additive A, the capacity retention rate of the lithium-ion battery after cycling at 25° C. and 45° C. showed an ascent and then showed a decline trend, and the thickness expansion rate after storage at 85° C. for 24 h was decreasing. This was because when the amount of the additive A was relatively large, the complex layer formed by the additive A being adsorbed on the surface of the positive active material was likely to be thicker and denser, affecting diffusion and migration of lithium ions, and greatly increasing positive electrode impedance. Secondly, the additive A consumed lithium ions while forming the complex layer, reducing lithium ions available for cycling. Finally, a relatively large amount of the additive A caused an increase in overall viscosity of the electrolyte and a decrease in an ionic conductivity, so that the capacity retention rate of the lithium-ion battery after cycling at 25° C. and 45° C. showed an ascent and then showed a decline trend. Therefore, the amount of the additive A needs to be appropriate. Preferably, the amount is 0.1%-10%; more preferably, is 0.1%-6%; further more preferably, is 0.1%-3.5%.

It can be seen from Examples 8-14 that when an end-of-charge voltage was fixed at 4.35 V, with an increase (from 0.1% to 10%) in the amount of the additive B, the capacity retention rate of the lithium-ion battery after cycling at 25° C. and 45° C. showed an ascent and then showed a decline trend, and the thickness expansion rate after storage at 85° C. for 24 h was decreasing. This was because when the additive B was added in a large amount, it has a stronger repairing effect on the complex layer on the surface of the positive active material, and the complex layer formed on the surface of the positive active material is likely to be thicker and denser, the positive and negative electrode impedances increase significantly, so that the capacity retention rate of the lithium-ion battery after cycling at 25° C. and 45° C. showed an ascent and then showed a decline trend. Therefore, the amount of the additive B also needs to be appropriate. Preferably, the amount is 0.1%-10.0%; more preferably, is 0.1%-5.0%.

According to the disclosure and guidance in this specification, a person skilled in the art to which this application relates may also make appropriate changes and modifications to the foregoing embodiments. Therefore, this application is not limited to the specific embodiments disclosed and described above, and modifications and changes to the present application shall also fall within the protection scope of the claims of this application. In addition, although some specific terms are used in this specification, these terms are merely intended for ease of description, and do not constitute any limitation on this application.

What is claimed is:

1. A lithium-ion battery, comprising an electrode assembly and an electrolyte, the electrode assembly comprising a positive electrode sheet, a negative electrode sheet and a separation film;
   wherein
   a positive active material in the positive electrode sheet comprises $Li_{x1}Co_{y1}M_{1-y1}O_{2-z1}Q_{z1}$, $0.5 \leq x1 \leq 1.2$, $0.8 \leq y1 < 1.0$, $0 \leq z1 \leq 0.1$, M is selected from one or more of the group consisting of Al, Ti, Zr, Y, and Mg, and Q is selected from one or more of the group consisting of F, Cl, and S;
   the electrolyte also contains an additive A and an additive B, the additive A is selected from one or more of the group consisting of compounds represented by Formula I-1, and Formula 1-3, and the additive B is selected from one or more of the group consisting of compounds represented by Formula II-1 and Formula II-2;

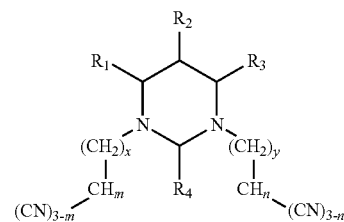

Formula I-1

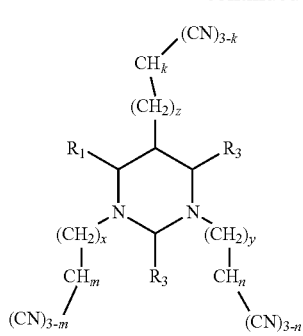
Formula I-3 in Formula I-1 and Formula I-3: $R_1$, $R_2$, $R_3$, and $R_4$ are each independently selected from the group consisting of a hydrogen atom, a halogen atom, a substituted or unsubstituted $C_1$-$C_{12}$ alkyl group, a substituted or unsubstituted $C_1$-$C_{12}$ alkoxy group, a substituted or unsubstituted $C_1$-$C_{12}$ amine group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, and a substituted or unsubstituted $C_2$-$C_{12}$ heterocyclic group, wherein a substituent group is selected from one or more of the group consisting of a halogen atom, a nitrile group, a C1-C6 alkyl group, a $C_2$-$C_6$ alkenyl group, and a $C_1$-$C_6$ alkoxy group; x, y, z are each independently selected from integers of 0-8; and m, n, k are each independently selected from integers of 0-2;

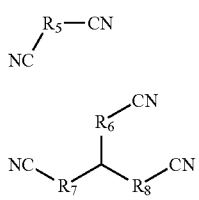

Formula II-1

Formula II-2 in Formula II-1 and Formula II-2: $R_5$ is selected from the group consisting of a substituted or unsubstituted $C_1$-$C_{12}$ alkylene group, a substituted or unsubstituted $C_2$-$C_{12}$ alkenylene group, and a substituted or unsubstituted $C_2$-$C_{12}$ alkynylene group, and $R_6$, $R_7$, and $R_8$ are each independently selected from the group consisting of substituted or unsubstituted $C_0$-$C_{12}$ alkylene group, substituted or unsubstituted $C_2$-$C_{12}$ alkenylene group, and substituted or unsubstituted $C_2$-$C_{12}$ alkynylene group, wherein a substituent group is selected from one or more of the group consisting of a halogen atom, a nitrile group, a $C_1$-$C_6$ alkyl group, a $C_2$-$C_6$ alkenyl group, and a $C_1$-$C_6$ alkoxy group;

a mass percentage of the additive A in the electrolyte is 0.1% to 3.5% and a mass percentage of the additive B in the electrolyte is 0.1% to 5%.

2. The lithium-ion battery according to claim 1, wherein in Formula I-1 and Formula I-3: $R_1$, $R_2$, $R_3$, and $R_4$ are each independently selected from the group consisting of a hydrogen atom, a halogen atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxy group, a substituted or unsubstituted $C_1$-$C_3$ amine group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, and a substituted or unsubstituted $C_2$-$C_7$ heterocyclic group, wherein a substituent group is selected from halogen atoms; and/or, in Formula II-1 and Formula II-2: $R_5$ is selected from the group consisting of a substituted or unsubstituted $C_1$-$C_{10}$ alkylene group, a substituted or unsubstituted $C_2$-$C_{10}$ alkenylene group, and a substituted or unsubstituted $C_2$-$C_{10}$ alkynylene group, and $R_6$, $R_7$, and $R_8$ are each independently selected from the group consisting of a substituted or unsubstituted $C_0$-$C_{10}$ alkylene group, a substituted or unsubstituted $C_2$-$C_{10}$ alkenylene group, and a substituted or unsubstituted $C_2$-$C_{10}$ alkynylene group, wherein a substituent group is selected from halogen atoms.

3. The lithium-ion battery according to claim 1, wherein in Formula I-1 and Formula I-3: x, y, and z are each independently selected from 0, 1 or 2; and m, n, and k are each independently selected from 1 or 2.

4. The lithium-ion battery according to claim 1, wherein in Formula I-1, $R_1$, $R_3$ and $R_4$ are all hydrogen atoms; and in Formula I-3, at least two of $R_1$, $R_2$, and $R_3$ are hydrogen atoms.

5. The lithium-ion battery according to claim 1, wherein in Formula II-1, $R_5$ is selected from the group consisting of a $C_2$-$C_4$ alkylene group, a $C_2$-$C_4$ alkenylene group, and a $C_2$-$C_4$ alkynylene group; and in Formula II-2, $R_6$ is selected from a $C_0$-$C_1$ alkylene group, $R_7$ and $R_8$ are each independently selected from the group consisting of a $C_2$-$C_4$ alkylene group, a $C_2$-$C_4$ alkenylene group, and a $C_2$-$C_4$ alkynylene group.

6. The lithium-ion battery according to claim 1, wherein the additive A is selected from one or more of following compounds:

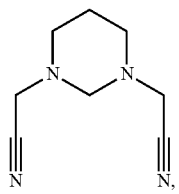
Formula I-1(1)

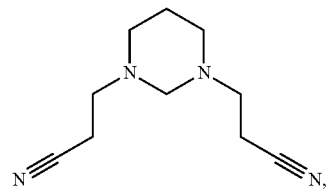
Formula I-1(2)

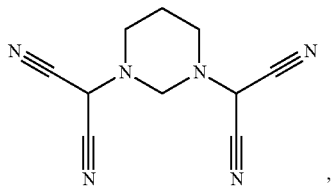
Formula I-1(3)

Formula I-1(4)
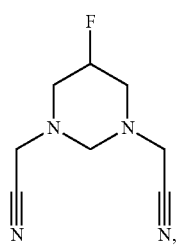
Formula I-1(5)
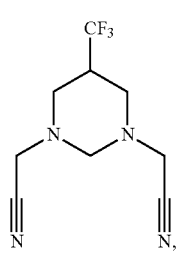
Formula I-1(6)
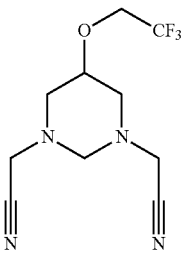
Formula I-1(7)
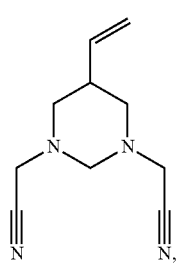
Formula I-1(8)
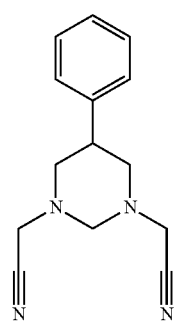
Formula I-1(9)
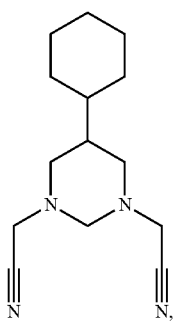
Formula I-1(10)
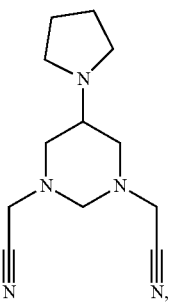
Formula I-1(11)
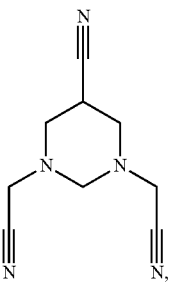
Formula I-1(12)
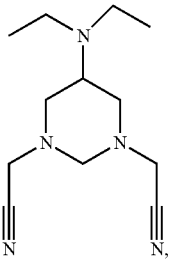
Formula I-1(13)
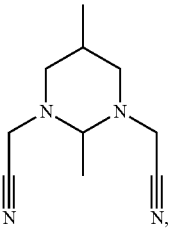
Formula I-1(14)
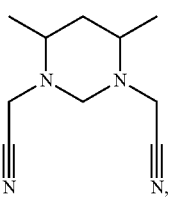

-continued

Formula I-3(1)

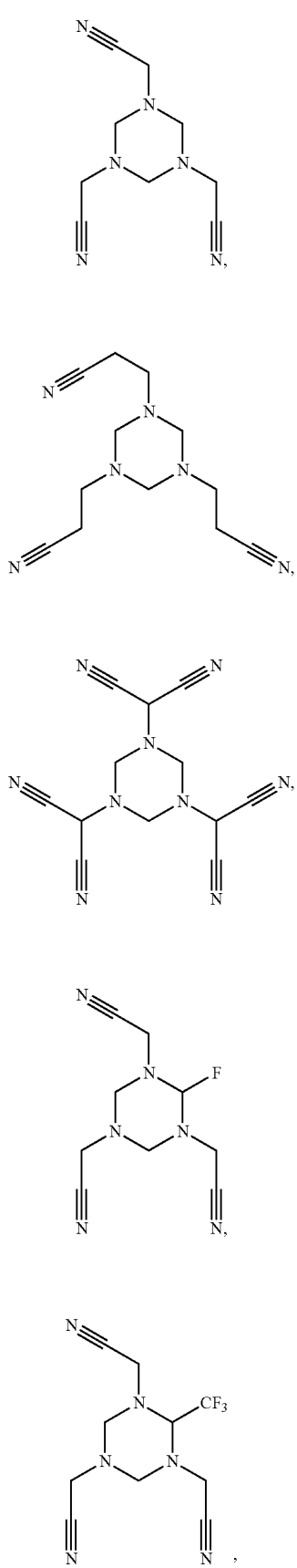

Formula I-3(2)

Formula I-3(3)

Formula I-3(4)

Formula I-3(5)

Formula I-3(6)

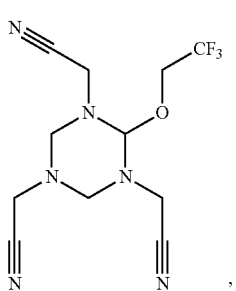

Formula I-3(7)

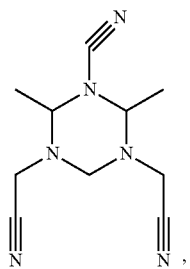

Formula I-3(8)

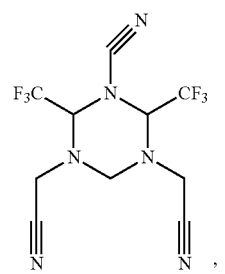

Formula I-3(9)

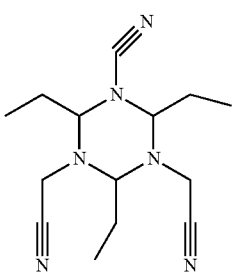

7. The lithium-ion battery according to claim 1, wherein the additive B is selected from one or more of the group consisting of succinonitrile, glutaronitrile, adiponitrile, pimelic nitrile, suberonitrile, azelaonitrile, sebaconitrile, undecane dinitrile, dodecane dinitrile, tetramethyl succinate nitrile, methyl glutaronitrile, butenedinitrile, 2-pentenedinitrile, hex-2-enedinitrile, hex-3-enedinitrile, oct-4-enedinitrile, oct-4-enedinitrile nitrile, 1,2,3-propanetricarbonitrile, 1,3,5-pentanetricarbonitrile, and 1,3,6-hexanetricarbonitrile.

8. The lithium-ion battery according to claim 1, wherein the electrolyte further contains an additive C, which is selected from one or more of the group consisting of a cyclic carbonate compound containing a carbon-carbon unsaturated bond, a halogen-substituted cyclic carbonate compound, a sulfate ester compound, a sultone compound, a disulfonate compound, a sulfite compound, an aromatic compound, an isocyanate compound, a phosphazene compound, an acid anhydride compound, a phosphite compound, a phosphate compound, and a borate compound; and a mass percentage of the additive C in the electrolyte is 0.01%-30%.

9. The lithium-ion battery according to claim 1, wherein the negative active material in the negative electrode sheet is selected from one or more of the group consisting of soft carbon, hard carbon, artificial graphite, natural graphite, Si, $SiOx_2$, Si/C composite material, Si alloy, lithium titanate and metal capable of forming an alloy with lithium, $0<x2\leq2$.

10. An apparatus, comprising the lithium-ion battery according to claim 1.

\* \* \* \* \*